(12) United States Patent
Pitterna et al.

(10) Patent No.: US 8,822,502 B2
(45) Date of Patent: *Sep. 2, 2014

(54) INSECTICIDAL COMPOUNDS

(75) Inventors: Thomas Pitterna, Stein (CH); Myriem El Qacemi, Stein (CH); Vladimir Bobosik, Bratislava (SK); Peter Renold, Stein (CH); Jérôme Yves Cassayre, Stein (CH); Pierre Joseph Marcel Jung, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 334 days.

This patent is subject to a terminal disclaimer.

(21) Appl. No.: 13/060,218

(22) PCT Filed: Jul. 24, 2009

(86) PCT No.: PCT/EP2009/059562
§ 371 (c)(1),
(2), (4) Date: Mar. 25, 2011

(87) PCT Pub. No.: WO2010/020521
PCT Pub. Date: Feb. 25, 2010

(65) Prior Publication Data
US 2011/0166184 A1    Jul. 7, 2011

(30) Foreign Application Priority Data

Aug. 22, 2008  (GB) .................. 0815437.9
Jan. 14, 2009  (GB) .................. 0900561.2
Mar. 20, 2009  (GB) .................. 0904868.7
Jun. 22, 2009  (GB) .................. 0910771.5

(51) Int. Cl.
*A01N 43/80*    (2006.01)
*C07D 261/02*   (2006.01)
*C07D 413/12*   (2006.01)

(52) U.S. Cl.
USPC ......... 514/340; 514/378; 546/272.1; 548/240

(58) Field of Classification Search
None
See application file for complete search history.

(56) References Cited

U.S. PATENT DOCUMENTS

2007/0066617 A1  3/2007  Mita et al.
2012/0015946 A1* 1/2012  Renold et al. ............... 514/236.8

FOREIGN PATENT DOCUMENTS

| | | |
|---|---|---|
| EP | 1538138 | 6/2005 |
| EP | 1731512 | 12/2006 |
| EP | 1731512 A1 | 12/2006 |
| EP | 1932836 | 6/2008 |
| EP | 2151437 A1 | 2/2010 |
| EP | 2172448 A1 | 4/2010 |
| EP | 2172462 A1 | 4/2010 |
| JP | 2008239611 | 10/2008 |
| JP | 2009108046 | 5/2009 |
| JP | 2010083883 | 4/2010 |
| JP | 2010168367 | 8/2010 |
| WO | 2004018410 | 3/2004 |
| WO | 2007070606 | 6/2007 |
| WO | 2007075459 | 7/2007 |
| WO | 2007079162 | 7/2007 |
| WO | 2007080131 | 7/2007 |
| WO | 2007093402 | 8/2007 |
| WO | 2008154528 | 12/2008 |
| WO | 2009002809 | 12/2008 |
| WO | 2009003075 | 12/2008 |
| WO | 2009024541 | 2/2009 |
| WO | 2009025983 | 2/2009 |
| WO | 2009063910 | 5/2009 |
| WO | 2009080250 | 7/2009 |
| WO | 2010003877 | 1/2010 |
| WO | 2010003923 | 1/2010 |
| WO | 2010005048 | 1/2010 |
| WO | 2010020521 | 2/2010 |
| WO | 2010020522 | 2/2010 |
| WO | 2010025998 | 3/2010 |
| WO | 2010079077 | 7/2010 |
| WO | 2010084067 | 7/2010 |
| WO | 2010086225 | 8/2010 |
| WO | 2010108733 | 9/2010 |
| WO | 2010125130 | 11/2010 |
| WO | 2010149506 | 12/2010 |

OTHER PUBLICATIONS

Diggle A W et al: "Pathways in fission of strained rings", Bulletin De La Societe Chimique De France, Societe Francaise De Chimie, Paris, France, Jan. 1, 1988, pp. 317-321.

* cited by examiner

*Primary Examiner* — Kamal Saeed
(74) *Attorney, Agent, or Firm* — R. Kody Jones

(57) ABSTRACT

A compound of formula (I): wherein $A^1, A^2, A^3, A^4, A^{1'}, A^{2'}, A^{3'}, A^{4'}, A^{5'}, A^{6'}, G^1, R^1, R^2, R^3, R^4, R^{5a}$ and $R^{5b}$ are as defined in claim 1; or a salt or N-oxide thereof. Furthermore, the present invention relates to processes and intermediates for preparing compounds of formula (I) or compounds of formula (I'), to insecticidal, acaricidal, nematicidal and molluscicidal compositions comprising compounds of formula (I) or compounds of formula (I'), and to methods of using compounds of formula (I) or compounds of formula (I') to combat and control insect, acarine, nematode and mollusc pests.

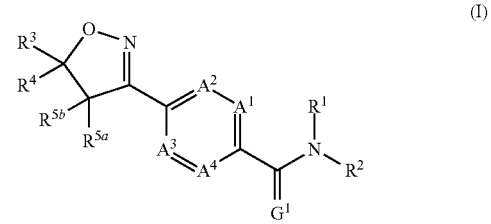

(I)

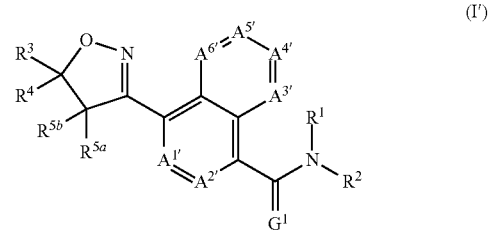

(I')

19 Claims, No Drawings

INSECTICIDAL COMPOUNDS

This application is a 371 of International Application No. PCT/EP2009/059562 filed Jul. 24, 2009, which claims priority to GB 0815437.9 filed Aug. 22, 2008, GB 0900561.2 filed Jan. 14, 2009, GB 0904868.7 filed Mar. 20, 2009, and GB 0910771.5 filed Jun. 22, 2009, the contents of which are incorporated herein by reference.

The present invention relates to certain benzamide isoxazolines, to processes and intermediates for preparing them, to insecticidal, acaricidal, nematicidal and molluscicidal compositions comprising them and to methods of using them to combat and control insect, acarine, nematode and mollusc pests.

Certain isoxazoline derivatives with insecticidal properties are disclosed, for example, in EP 1,731,512, US 2007/066617, JP 2007/008914, JP 2007/016017, WO 07/026,965, JP 2007/106756, WO 07/070,606, WO 07/074,789 and WO 07/075,459.

It has now surprisingly been found that certain benzamide isoxazolines with one or two substituents in 4-position of the isoxazoline ring have insecticidal properties.

The present invention therefore provides a compound of formula (I) or a compound of formula (I')

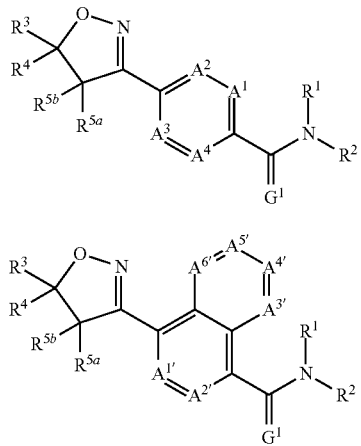

wherein
$A^1$, $A^2$, $A^3$ and $A^4$, or $A^{1'}$, $A^{2'}$, $A^{3'}$, $A^{4'}$, $A^{5'}$, and $A^{6'}$, are independently of each other C—H, C—$R^6$, or nitrogen;
$G^1$ is oxygen or sulfur;
$R^1$ is hydrogen, $C_1$-$C_8$alkyl, $C_1$-$C_8$alkoxy, $C_1$-$C_8$alkylcarbonyl-, or $C_1$-$C_8$alkoxycarbonyl-;
$R^2$ is $C_1$-$C_8$alkyl or $C_1$-$C_8$alkyl substituted by one to five $R^7$, aryl-$C_1$-$C_4$alkylene- or aryl-$C_1$-$C_4$alkylene- wherein the aryl moiety is substituted by one to five $R^8$, heterocyclyl-$C_1$-$C_4$alkylene- or heterocyclyl-$C_1$-$C_4$alkylene- wherein the heterocyclyl moiety is substituted by one to five $R^8$, $C_3$-$C_{10}$cycloalkyl, $C_3$-$C_{10}$halocycloalkyl, aryl or aryl substituted by one to five $R^8$, or heterocyclyl or heterocyclyl substituted by one to five $R^8$;
$R^3$ is $C_1$-$C_8$haloalkyl;
$R^4$ is aryl or aryl substituted by one to five $R^9$, or heteroaryl or heteroaryl substituted by one to five $R^9$;
$R^{5a}$ and $R^{5b}$ are, independently of each other, hydrogen, cyano, halogen, $C_1$-$C_8$alkylthio-, $C_1$-$C_8$ haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, arylthio- or arylthio- wherein the aryl moiety is substituted by one to five $R^{10}$, arylsulfinyl- or arylsulfinyl- wherein the aryl moiety is substituted by one to five $R^{10}$, arylsulfonyl- or arylsulfonyl- wherein the aryl moiety is substituted by one to five $R^{10}$, heterocyclylthio- or heterocyclylthio- wherein the heterocyclyl moiety is substituted by one to five $R^{10}$, heterocyclylsulfinyl- or heterocyclylsulfinyl- wherein the heterocyclyl moiety is substituted by one to five $R^{10}$, or heterocyclylsulfonyl- or heterocyclylsulfonyl- wherein the heterocyclyl moiety is substituted by one to five $R^{10}$, $C_1$-$C_8$alkyl, $C_2$-$C_8$alkenyl, $C_2$-$C_8$alkynyl, $C_1$-$C_8$haloalkyl, $C_2$-$C_8$haloalkenyl, hydroxy, $C_1$-$C_8$alkoxy, $C_3$-$C_8$alkenyloxy, $C_3$-$C_8$alkynyloxy, or $C_1$-$C_8$haloalkoxy, provided that at least one of $R^{5a}$ and $R^{5b}$ is not hydrogen;
$R^{5a}$ and $R^{5b}$ may also be $C_1$-$C_8$alkyl substituted by one to five $R^7$;
each $R^7$ is independently halogen, cyano, nitro, $C_3$-$C_{10}$cycloalkyl, $C_3$-$C_{10}$halocycloalkyl, hydroxy, $C_1$-$C_8$alkoxy, $C_1$-$C_8$haloalkoxy, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$ haloalkylsulfonyl-; and
each $R^6$, $R^8$, $R^9$ and $R^{10}$ is independently halogen, cyano, nitro, $C_1$-$C_8$alkyl, $C_1$-$C_8$haloalkyl, $C_3$-$C_{10}$cycloalkyl, $C_3$-$C_{10}$halocycloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio-, $C_1$-$C_8$haloalkylthio-, $C_1$-$C_8$alkylsulfinyl-, $C_1$-$C_8$ haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl itself substituted by one to five substituents independently selected from halogen, $C_1$-$C_4$alkyl, $C_1$-$C_4$haloalkyl, $C_1$-$C_4$alkoxy, or $C_1$-$C_4$haloalkoxy, or heterocyclyl or heterocyclyl itself substituted by one to five substituents independently selected from halogen, $C_1$-$C_4$alkyl, $C_1$-$C_4$haloalkyl, $C_1$-$C_4$alkoxy, or $C_1$-$C_4$haloalkoxy;
or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

The compounds of the invention may contain one or more asymmetric carbon atoms, for example, at the —$CR^3R^4$— group and the —$CR^{5a}R^{5b}$— group, or at the $LR^2Y^1Y^3$ group (see below) and may exist as enantiomers (or as pairs of diastereoisomers) or as mixtures of such.

Each alkyl moiety either alone or as part of a larger group (such as alkoxy, alkylthio, alkylcarbonyl, or alkoxycarbonyl) is a straight or branched chain and is, for example, methyl, ethyl, n-propyl, prop-2-yl, n-butyl, but-2-yl, 2-methyl-prop-1-yl or 2-methyl-prop-2-yl. The alkyl groups are preferably $C_1$ to $C_6$ alkyl groups, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Each alkylene moiety is a straight or branched chain and is, for example, —$CH_2$—, —$CH_2$—$CH_2$—, —$CH(CH_3)$—, —$CH_2$—$CH_2$—$CH_2$—, —$CH(CH_3)$—$CH_2$—, or —$CH(CH_2CH_3)$—. The alkylene groups are preferably $C_1$ to $C_3$ alkylene groups, more preferably $C_1$-$C_2$, most preferably $C_1$ alkylene groups.

Alkenyl moieties can be in the form of straight or branched chains, and the alkenyl moieties, where appropriate, can be of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups.

Alkynyl moieties can be in the form of straight or branched chains. Examples are ethynyl and propargyl. The alkynyl groups are preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy or haloalkylthio) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups, respectively, which are substituted with one or more of the same or different halogen atoms and are, for example, 2,2-difluoro-vinyl or 1,2-dichloro-2-fluoro-vinyl.

Haloalkynyl groups are alkynyl groups, respectively, which are substituted with one or more of the same or different halogen atoms and are, for example, 1-chloro-prop-2-ynyl.

Cycloalkyl groups can be in mono- or bi-cyclic form and may optionally be substituted by one or more methyl groups. The cycloalkyl groups preferably contain 3 to 8 carbon atoms, more preferably 3 to 6 carbon atoms. Examples of monocyclic cycloalkyl groups are cyclopropyl, cyclobutyl, cyclohexyl and 2-methyl-cyclohex-1-yl. An example of a bicyclic cycloalkyl group is bicyclo[2.2.1]heptan-2-yl.

Halocycloalkyl groups are cycloalkyl groups which are substituted with one or more of the same of different halogen atoms and may optionally be substituted by one or more methyl groups. Examples of monocyclic halocycloalkyl groups are 2,2-dichloro-cyclopropyl, 2,2-dichloro-1-methylcyclopropyl and 2-chloro-4-fluoro-cyclohexyl.

In the context of the present specification the term "aryl" refers to a ring system which may be mono-, bi- or tricyclic. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

The term "heteroaryl" refers to an aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl and thiadiazolyl. Examples of bicyclic groups include quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

The term "heterocyclyl" is defined to include heteroaryl and in addition their unsaturated or partially unsaturated analogues. Examples of monocyclic groups include thietanyl, pyrrolidinyl, tetrahydro-furanyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydrobenzofuranyl, benzo[1,3]dioxolanyl, and 2,3-dihydro-benzo[1,4]dioxinyl. Where a heterocyclyl moiety is said to be substituted, the heterocyclyl moiety is preferably substituted by one to four substituents, most preferably by one to three substituents.

Preferred values of $A^1, A^2, A^3, A^4, A^{1'}, A^{2'}, A^{3'}, A^{4'}, A^{5'}, A^{6'}, G^1, R^1, R^2, R^3, R^4, R^{5a}, R^{5b}, R^6, R^7, R^8, R^9,$ and $R^{10}$ are, in any combination, as set out below.

Preferably no more than two of $A^1$, $A^2$, $A^3$ and $A^4$ are nitrogen.

Preferably $A^1$ is C—H or C—$R^6$, most preferably $A^1$ is C—$R^6$.

Preferably $A^2$ is C—H or C—$R^6$, most preferably $A^2$ is C—H.

Preferably $A^3$ is C—H or C—$R^6$, most preferably $A^3$ is C—H.

Preferably $A^4$ is C—H or C—$R^6$, most preferably $A^4$ is C—H.

Preferably no more than two of $A^{1'}, A^{2'}, A^{3'}, A^{4'}, A^{5'}$ and $A^{6'}$ are nitrogen.

Preferably $A^{1'}$ is C—H or C—$R^6$, most preferably $A^{1'}$ is C—H.

Preferably $A^{2'}$ is C—H or C—$R^6$, most preferably $A^{2'}$ is C—H.

Preferably $A^{3'}$ is C—H or C—$R^6$, most preferably $A^{3'}$ is C—H.

Preferably $A^{4'}$ is C—H or C—$R^6$, most preferably $A^{4'}$ is C—H.

Preferably $A^{5'}$ is C—H or C—$R^6$, most preferably $A^{5'}$ is C—H.

Preferably $A^{6'}$ is C—H or C—$R^6$, most preferably $A^{6'}$ is C—H.

Preferably $G^1$ is oxygen.

Preferably $R^1$ is hydrogen, methyl, ethyl, methylcarbonyl-, or methoxycarbonyl-, more preferably hydrogen, methyl or ethyl, even more preferably hydrogen or methyl, most preferably hydrogen.

Preferably $R^2$ is $C_1$-$C_8$alkyl or $C_1$-$C_8$alkyl substituted by one to five $R^7$, phenyl-$C_1$-$C_4$alkylene- or phenyl-$C_1$-$C_4$alkylene- wherein the phenyl moiety is substituted by one to five $R^8$, pyridyl-$C_1$-$C_4$alkylene- or pyridyl-$C_1$-$C_4$alkylene- wherein the pyridyl moiety is substituted by one to five $R^8$, $C_3$-$C_{10}$cycloalkyl, $C_3$-$C_{10}$halocycloalkyl, oxetanyl or oxetanyl substituted by one to five $R^8$, thietanyl or thietanyl substituted by one to five $R^8$, oxo-thietanyl or oxo-thietanyl substituted by one to five $R^8$, or dioxo-thietanyl or dioxo-thietanyl substituted by one to five $R^8$, more preferably $C_1$-$C_8$alkyl or $C_1$-$C_8$alkyl substituted by one to three halogen atoms, phenyl-$C_1$-$C_4$alkylene- or phenyl-$C_1$-$C_4$alkylene- wherein the phenyl moiety is substituted by one to five $R^8$, pyridyl-$C_1$-$C_4$alkylene- or pyridyl-$C_1$-$C_4$alkylene- wherein the pyridyl moiety is substituted by one to five $R^8$, $C_3$-$C_{10}$cycloalkyl, thietanyl, oxo-thietanyl or dioxo-thietanyl, most preferably butyl-, 1-phenyl-eth-1-yl-, phenyl-methyl-, (pyrid-2-yl)-methyl-, cyclobutyl-, thietanyl-, oxo-thietanyl- or dioxo-thietanyl-. It is particularly preferred that the thietanyl, oxo-thietanyl or dioxo-thietanyl ring is linked via the 3-position.

A group of preferred compounds are those wherein $R^2$ is $C_1$-$C_6$alkyl or $C_1$-$C_6$alkyl substituted by one to five $R^7$, for example ethyl-, n-butyl-, but-2-yl-, 3-bromo-propyl-, 2,2,2-trifluoro-ethyl-, 3,3,3-trifluoro-propyl-, 2-methoxy-ethyl-, and 1-methoxy-prop-2-yl-.

A group of preferred compounds are those wherein $R^2$ is aryl-$C_1$-$C_2$alkylene- or aryl-$C_1$-$C_2$alkylene- wherein the aryl moiety is substituted by one to five $R^8$, for example phenylmethyl-, 1-phenyl-eth-1-yl-, 2-phenyl-eth-1-yl-, (3-chlorophenyl)-methyl-, (2-fluoro-phenyl)-methyl-, (4-methoxyphenyl)-methyl-, (2-trifluoromethyl-phenyl)-methyl-, and (2-trifluoromethoxy-phenyl)-methyl-.

A group of preferred compounds are those wherein $R^2$ is heterocyclyl-$C_1$-$C_2$alkylene- or heterocyclyl-$C_1$-$C_2$alkylene- wherein the heterocyclyl moiety is substituted by one to five $R^8$, for example (pyrid-2-yl)-methyl-, (pyrid-3-yl)-methyl-, (2-chloro-pyrid-5-yl)-methyl-, (1-methyl-1H-imidazol-4-yl)-methyl-, (furan-2-yl)-methyl-, 2-(thiophen-2'-yl)-eth-1-yl-, 2-(indol-3'-yl)-eth-1-yl-, (1H-benzimidazol-2-yl)-methyl-, (oxetan-2-yl)-methyl-, (tetrahydro-furan-2-yl)-methyl-, 2-([1',3']dioxolan-2'-yl)-eth-1-yl-, 2-(morpholin-4'-yl)-eth-1-yl-, 2-(benzo[1',3']dioxol-5'-yl)-eth-1-yl-, and (2,3-dihydro-benzo[1,4]dioxin-6-yl)-methyl-, more preferably $R^2$ is heteroaryl-$C_1$-$C_2$alkylene- or heteroaryl-$C_1$-$C_2$alkylene- wherein the heteroaryl moiety is substituted by one to five $R^8$.

A group of preferred compounds are those wherein $R^2$ is $C_3$-$C_8$cycloalkyl or $C_3$-$C_8$halocycloalkyl, for example cyclobutyl-, and 2-methyl-cyclohex-1-yl-.

A group of preferred compounds are those wherein $R^2$ is aryl or aryl substituted by one to five $R^8$, for example 2-chloro-phenyl-, 3-fluoro-phenyl-, 2-methyl-phenyl-, 2-chloro-6-methyl-phenyl-, 2-trifluoromethyl-phenyl-, and 2,4-dimethoxy-phenyl-.

A group of preferred compounds are those wherein $R^2$ is heterocyclyl or heterocyclyl substituted by one to five $R^8$, for example 3-methyl-pyrid-2-yl-, 1,3-dimethyl-1H-pyrazol-5-yl-, 4-methyl-thiazol-2-yl-, 5-methyl-thiadiazol-2-yl-, quinolin-2-yl-, quinolin-5-yl-, benzothiazol-6-yl-, 4-methyl-benzothiazol-2-yl-, thietan-3-yl-, 1-oxo-thietan-3-yl-, 1,1-dioxo-thietan-3-yl-, and 3-methyl-thietan-3-yl-, more preferably $R^2$ is thietanyl, oxo-thietanyl or dioxo-thietanyl each optionally substituted by one to five $R^8$, e.g. $R^2$ is oxo-thietanyl or dioxo-thietanyl each optionally substituted by one to five $R^8$. It is particularly preferred that the thietanyl, oxo-thietanyl or dioxo-thietanyl ring is linked via the 3-position.

Preferably $R^3$ is chlorodifluoromethyl or trifluoromethyl, most preferably trifluoro-methyl.

A group of preferred compounds are those wherein $R^4$ is aryl or aryl substituted by one to five $R^9$, more preferably $R^4$ is aryl substituted by two to three $R^9$, even more preferably $R^4$ is 3,5-dibromo-phenyl-, 3,5-dichloro-phenyl-, 3,4-dichloro-phenyl-, and 3,4,5-trichloro-phenyl-, most preferably $R^4$ is 3,5-dichloro-phenyl.

A group of preferred compounds are those wherein $R^4$ is heteroaryl or heteroaryl substituted by one to five $R^9$, most preferably $R^4$ is heteroaryl substituted by two to three $R^9$.

Preferably $R^{5a}$ is halogen, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkyl, $C_2$-$C_8$alkenyl, $C_2$-$C_8$alkynyl, $C_1$-$C_8$haloalkyl, $C_2$-$C_8$haloalkenyl, most preferably halogen, $C_1$-$C_8$alkylthio- or $C_1$-$C_8$alkyl. $R^{5a}$ may also be hydroxy.

Preferably $R^{5b}$ is halogen or hydrogen, most preferably hydrogen.

Preferably each $R^6$ is independently bromo, chloro, fluoro, cyano, nitro, methyl, ethyl, trifluoromethyl, methoxy, difluoromethoxy, or trifluoromethoxy, more preferably bromo, chloro, fluoro, nitro, or methyl, most preferably chloro, fluoro, or methyl.

Preferably each $R^7$ is independently halogen, cyano, nitro, hydroxy, $C_1$-$C_8$alkoxy, $C_1$-$C_8$haloalkoxy, mercapto, $C_1$-$C_8$alkylthio-, $C_1$-$C_8$haloalkylthio-, more preferably bromo, chloro, fluoro, methoxy, or methylthio, most preferably chloro, fluoro, or methoxy.

Preferably each $R^8$ is independently bromo, chloro, fluoro, cyano, nitro, methyl, ethyl, trifluoromethyl, methoxy, difluoromethoxy, or trifluoromethoxy, more preferably bromo, chloro, fluoro, nitro, or methyl, even more preferably chloro, fluoro, or methyl, most preferably methyl.

Preferably each $R^9$ is independently bromo, chloro, fluoro, trifluoromethyl, methoxy, or methylthio, more preferably bromo, chloro, fluoro, methoxy, or methylthio, most preferably bromo or chloro.

Preferably each $R^{10}$ is independently bromo, chloro, fluoro, cyano, nitro, methyl, ethyl, trifluoromethyl, methoxy, difluoromethoxy, or trifluoromethoxy, more preferably bromo, chloro, fluoro, nitro, or methyl, most preferably chloro, fluoro, or methyl.

A preferred embodiment are compounds of formula (I); or a salt or N-oxide thereof.

A preferred embodiment are compounds of formula (Ia) wherein $A^1$ is C-Me, $A^2$, $A^3$, and $A^4$ are C—H, $G^1$ is oxygen, $R^3$ is trifluoromethyl, $R^4$ is 3,5-dichloro-phenyl, $R^{5a}$ is bromo, $R^{5b}$ is hydrogen, and $R^1$ and $R^2$ are as defined for a compound of formula (I); or a salt or N-oxide thereof.

Preferably $R^2$ is group (z):

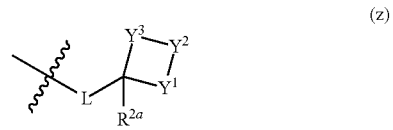

wherein L is a single bond or $C_1$-$C_6$ alkylene;
$R^{2a}$ is hydrogen, or $C_1$-$C_8$alkyl;
$Y^1$, $Y^2$ and $Y^3$ are independently of another $CR^{7a}R^{8a}$, C=O, C=N—$OR^{9a}$, N—$R^{9a}$, O, S, SO, $SO_2$, S=N—$R^{9a}$, or SO=N—$R^{9a}$, provided that at least one of $Y^1$, $Y^2$ or $Y^3$ is not $CR^{7a}R^{8a}$;
$R^{7a}$ and $R^{8a}$ are of another independently hydrogen, halogen, $C_1$-$C_8$alkyl, or $C_1$-$C_8$haloalkyl;
each $R^{9a}$ is independently hydrogen, cyano, nitro, $C_1$-$C_8$alkyl, $C_1$-$C_8$haloalkyl, $C_1$-$C_8$alkyl-carbonyl-, $C_1$-$C_8$haloalkylcarbonyl-, $C_1$-$C_8$alkoxycarbonyl-, $C_1$-$C_8$haloalkoxycarbonyl-, $C_1$-$C_8$alkylsulfonyl-, $C_1$-$C_8$haloalkylsulfonyl-, aryl-$C_1$-$C_4$alkyl- or aryl-$C_1$-$C_4$alkyl- wherein each aryl moiety is substituted by one to three $R^{11a}$, or is heteroaryl-$C_1$-$C_4$alkyl- or heteroaryl-$C_1$-$C_4$alkyl- wherein each heteroaryl moiety is substituted by one to three $R^{11a}$;
$R^{11a}$ is independently halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl-;

Preferably L is a single bond or $C_1$-$C_2$alkyl, yet even more preferably a single bond or methyl, most preferably a single bond.

Preferably $R^{2a}$ is hydrogen or methyl, most preferably hydrogen.

Preferably $Y^1$, $Y^2$ and $Y^3$ are independently of another $CR^{7a}R^{8a}$, C=O, C=N—$OR^{9a}$, N—$R^{9a}$, O, S, SO, $SO_2$, S=N—$R^{9a}$, or SO=N—$R^{9a}$, provided that only one of $Y^1$, $Y^2$ or $Y^3$ is not $CR^{7a}R^{8a}$.

More preferably $Y^1$, $Y^2$ and $Y^3$ are independently of another $CR^{7a}R^{8a}$, N—$R^{9a}$, O, S, SO, $SO_2$, S=N—$R^{9a}$, or SO=N—$R^{9a}$, provided that only one of $Y^1$, $Y^2$ or $Y^3$ is not $CR^{7a}R^{8a}$.

More preferably $Y^1$, $Y^2$ and $Y^3$ are independently of another $CR^7R^8$, O, S, SO, $SO_2$, S=N—$R^9$, or SO=N—$R^9$, provided that only one of $Y^1$, $Y^2$ or $Y^3$ is not $CR^7R^8$.

Even more preferably $Y^1$, $Y^2$ and $Y^3$ are independently of another $CR^{7a}R^{8a}$, O, S, SO, or $SO_2$, provided that only one of $Y^1$, $Y^2$ or $Y^3$ is not $CR^{7a}R^{8a}$, Even more preferably $Y^2$ is O, S, SO, or $SO_2$, and $Y^1$ and $Y^3$ are independently of another $CR^{7a}R^{8a}$.

Most preferably, $Y^2$ is S, SO, or $SO_2$, and $Y^1$ and $Y^3$ are independently of another $CR^{7a}R^{8a}$.

In one embodiment $Y^1$ is C=O, C=N—$OR^{9a}$, N—$R^{9a}$, O, S, SO, $SO_2$, S=N—$R^{9a}$, or SO=N—$R^{9a}$, and $Y^2$ and $Y^3$ are independently of another $CR^{7a}R^{8a}$.

In one embodiment $Y^2$ is C=O, C=N—$OR^{9a}$, N—$R^{9a}$, O, S, SO, $SO_2$, S=N—$R^{9a}$, or SO=N—$R^{9a}$, and $Y^1$ and $Y^3$ are independently of another $CR^{7a}R^{8a}$.

In one embodiment $Y^2$ is C=O, C=N—$OR^{9a}$, O, S, SO, $SO_2$, S=N—$R^{9a}$, or SO=N—$R^{9a}$, and $Y^1$ and $Y^3$ are independently of another $CR^{7a}R^{8a}$.

Preferably each $R^{7a}$ and $R^{8a}$ is independently hydrogen or methyl, most preferably hydrogen.

Preferably each $R^{9a}$ is independently hydrogen, cyano, methyl, trifluoromethyl, methylcarbonyl-, trifluoromethylcarbonyl-, methoxycarbonyl-, trifluoromethoxycarbonyl-, methylsulfonyl-, trifluoromethylsulfonyl-, or benzyl or benzyl wherein the phenyl moiety is substituted by one to three $R^{10a}$, most preferably each $R^{9a}$ is independently hydrogen, methyl, trifluoromethyl, or benzyl or benzyl wherein the phenyl moiety is substituted by one to three $R^{10a}$.

Preferably each $R^{10a}$ is independently bromo, chloro, fluoro, cyano, nitro, methyl, ethyl, trifluoromethyl, methoxy, difluoromethoxy, trifluoromethoxy, or methoxycarbonyl-, more preferably chloro, fluoro, cyano, nitro, methyl, ethyl, trifluoromethyl, methoxy, or trifluoromethoxy, most preferably each $R^{10a}$ is independently preferably bromo, chloro, or fluoro.

Preferably each $R^{11a}$ is independently bromo, chloro, fluoro, cyano, nitro, methyl, ethyl, trifluoromethyl, methoxy, difluoromethoxy, trifluoromethoxy, or methoxycarbonyl-, more preferably chloro, fluoro, cyano, nitro, methyl, ethyl, trifluoromethyl, methoxy, or trifluoromethoxy, most preferably each $R^{11a}$ is independently preferably bromo, chloro, or fluoro.

Preferably, L is a single bond;
$Y^1$, $Y^2$ and $Y^3$ are independently of another $CR^{7a}R^{8a}$, N—$R^{9a}$, O, S, SO, $SO_2$, S=N—$R^{9a}$, or SO=N—$R^{9a}$, provided that one of $Y^1$, $Y^2$ or $Y^3$ is not $CR^{7a}R^{8a}$;
$R^{2a}$ is hydrogen or methyl;
$R^{7a}$ and $R^{8a}$ are independently of another hydrogen, halogen $C_1$-$C_4$ alkyl or $C_1$-$C_4$ haloalkyl; and
$R^{9a}$ is hydrogen, halogen $C_1$-$C_4$ alkyl or $C_1$-$C_4$ haloalkyl.

A preferred embodiment are compounds of formula (Ib) wherein $A^1$ is C-Me, $A^2$, $A^3$, and $A^4$ are C—H, $G^1$ is oxygen, $R^3$ is trifluoromethyl, $R^4$ is 3,5-dichloro-phenyl, $R^{5a}$ is chloro, $R^{5b}$ is hydrogen, and $R^1$ and $R^2$ are as defined for a compound of formula (I); or a salt or N-oxide thereof.

A preferred embodiment are compounds of formula (Ic) wherein $A^1$ is C-Me, $A^2$, $A^3$, and $A^4$ are C—H, $G^1$ is oxygen, $R^3$ is trifluoromethyl, $R^4$ is 3,5-dichloro-phenyl, $R^{5a}$ and $R^{5b}$ are fluoro, and $R^1$ and $R^2$ are as defined for a compound of formula (I), preferably wherein $R^2$ is group (z); or a salt or N-oxide thereof.

A preferred embodiment are compounds of formula (Id.1) wherein $A^1$ is C-Me, $A^2$, $A^3$, and $A^4$ are C—H, $G^1$ is oxygen, $R^3$ is trifluoromethyl, $R^4$ is 3,5-dichloro-phenyl, $R^{5a}$ is methylthio-, $R^{5b}$ is hydrogen, and $R^1$ and $R^2$ are as defined for a compound of formula (I) preferably wherein $R^2$ is group (z); or a salt or N-oxide thereof.

A preferred embodiment are compounds of formula (Id.2) wherein $A^1$ is C-Me, $A^2$, $A^3$, and $A^4$ are C—H, $G^1$ is oxygen, $R^3$ is trifluoromethyl, $R^4$ is 3,5-dichloro-phenyl, $R^{5a}$ is methylsulfonyl-, $R^{5b}$ is hydrogen, and $R^1$ and $R^2$ are as defined for a compound of formula (I), preferably wherein $R^2$ is group (z); or a salt or N-oxide thereof.

A preferred embodiment are compounds of formula (Ie) wherein $A^1$ is C-Me, $A^2$, $A^3$, and $A^4$ are C—H, $G^1$ is oxygen, $R^3$ is trifluoromethyl, $R^4$ is 3,5-dichloro-phenyl, $R^{5a}$ is methyl, $R^{5b}$ is hydrogen, and $R^1$ and $R^2$ are as defined for a compound of formula (I), preferably wherein $R^2$ is group (z); or a salt or N-oxide thereof.

A preferred embodiment are compounds of formula (Ig) wherein $A^1$ is C-Me, $A^2$, $A^3$, and $A^4$ are C—H, $G^1$ is oxygen, $R^3$ is trifluoromethyl, $R^4$ is 3,5-dichloro-phenyl, $R^{5a}$ is fluoro, $R^{5b}$ is hydrogen, and $R^1$ and $R^2$ are as defined for a compound of formula (I), preferably wherein $R^2$ is group (z); or a salt or N-oxide thereof.

A preferred embodiment are compounds of formula (Ih) wherein $A^1$ is C-Me, $A^2$, $A^3$, and $A^4$ are C—H, $G^1$ is oxygen, $R^3$ is trifluoromethyl, $R^4$ is 3,5-dichloro-phenyl, $R^{5a}$ is hydroxy, $R^{5b}$ is hydrogen, and $R^1$ and $R^2$ are as defined for a compound of formula (I), preferably wherein $R^2$ is group (z); or a salt or N-oxide thereof.

A preferred embodiment are compounds of formula (I'); or a salt or N-oxide thereof.

A preferred embodiment are compounds of formula (I'a) wherein $A^{1'}$, $A^{2'}$, $A^{3'}$, $A^{4'}$, $A^{5'}$ and $A^{6'}$ are C—H, $G^1$ is oxygen, $R^3$ is trifluoromethyl, $R^4$ is 3,5-dichloro-phenyl, $R^{5a}$ is bromo, $R^{5b}$ is hydrogen, and $R^1$ and $R^2$ are as defined for a compound of formula (I'), preferably wherein $R^2$ is group (z); or a salt or N-oxide thereof.

In one embodiment the invention provides a compound of formula (I)

In one embodiment the invention provides a compound of formula (I').

Certain intermediates form a further aspect of the invention. One group of intermediates are compounds of formula (II) or compounds of formula (II')

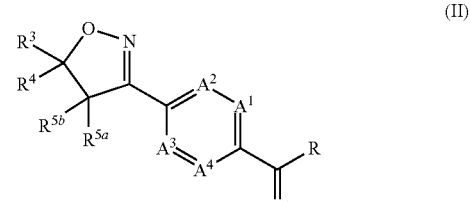

(II)

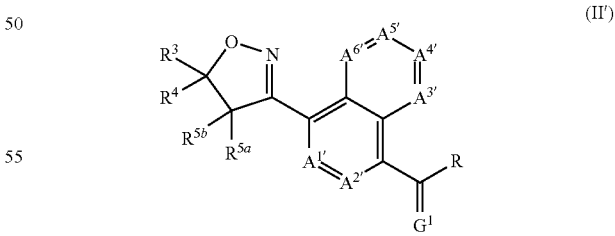

(II')

wherein $A^1$, $A^2$, $A^3$, $A^4$, $A^{1'}$, $A^{2'}$, $A^{3'}$, $A^{4'}$, $A^{5'}$, $A^{6'}$, $R^3$, $R^4$, $R^{5a}$ and $R^{5b}$ are as defined for a compound of formula (I), $G^1$ is oxygen, and R is hydroxy, $C_1$-$C_6$alkoxy or halogen, such as bromo, chloro or fluoro; or a salt or N-oxide thereof. The preferences for $A^1$, $A^2$, $A^3$, $A^4$, $A^{1'}$, $A^{2'}$, $A^{3'}$, $A^{4'}$, $A^{5'}$, $A^{6'}$, $R^3$, $R^4$, $R^{5a}$ and $R^{5b}$ are the same as the preferences set out for the corresponding substituents of a compound of formula (I). Preferably R is hydroxy, $C_1$-$C_6$alkoxy or chloro.

In one embodiment the invention provides a compound of formula (II).

In another embodiment the invention provides a compound of formula (II').

Furthermore, the present invention therefore provides a compound of formula (I")

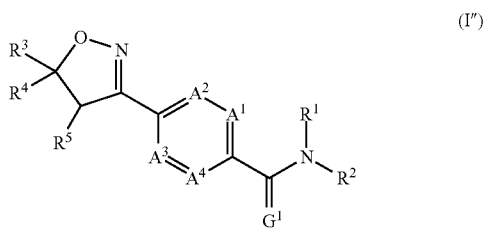

(I")

wherein
A$^1$, A$^2$, A$^3$ and A$^4$ are independently of each other C—H, C—R$^6$, or nitrogen;
G$^1$ is oxygen or sulfur;
R$^1$ is hydrogen, C$_1$-C$_8$alkyl, C$_1$-C$_8$alkylcarbonyl-, or C$_1$-C$_8$alkoxycarbonyl-;
R$^2$ is C$_1$-C$_8$alkyl or C$_1$-C$_8$alkyl substituted by one to five R$^7$, aryl-C$_1$-C$_4$alkylene- or aryl-C$_1$-C$_4$alkylene- wherein the aryl moiety is substituted by one to five R$^8$, heterocyclyl-C$_1$-C$_4$alkylene- or heterocyclyl-C$_1$-C$_4$alkylene- wherein the heterocyclyl moiety is substituted by one to five R$^8$, C$_3$-C$_{10}$cycloalkyl, C$_3$-C$_{10}$halocycloalkyl, aryl or aryl substituted by one to five R$^8$, or heterocyclyl or heterocyclyl substituted by one to five R$^8$;
R$^3$ is C$_1$-C$_8$haloalkyl;
R$^4$ is aryl or aryl substituted by one to five R$^9$, or heteroaryl or heteroaryl substituted by one to five R$^9$;
R$^5$ is halogen, C$_1$-C$_8$alkylthio-, C$_1$-C$_8$haloalkylthio-, C$_1$-C$_8$alkylsulfinyl-, C$_1$-C$_8$haloalkylsulfinyl-, C$_1$-C$_8$alkylsulfonyl-, C$_1$-C$_8$haloalkylsulfonyl-, arylthio- or arylthio- wherein the aryl moiety is substituted by one to five R$^{10}$, arylsulfinyl- or arylsulfinyl- wherein the aryl moiety is substituted by one to five R$^{10}$, arylsulfonyl- or arylsulfonyl- wherein the aryl moiety is substituted by one to five R$^{10}$, heterocyclylthio- or heterocyclylthio- wherein the heterocyclyl moiety is substituted by one to five R$^{10}$, heterocyclylsulfinyl- or heterocyclylsulfinyl- wherein the heterocyclyl moiety is substituted by one to five R$^{10}$, or heterocyclylsulfonyl- or heterocyclylsulfonyl- wherein the heterocyclyl moiety is substituted by one to five R$^{10}$;
R$^5$ may also be hydroxy;
each R$^6$ is independently halogen, cyano, nitro, C$_1$-C$_8$alkyl, C$_1$-C$_8$haloalkyl, C$_2$-C$_8$alkenyl, C$_2$-C$_8$haloalkenyl, C$_2$-C$_8$alkynyl, C$_2$-C$_8$haloalkynyl, hydroxy, C$_1$-C$_8$alkoxy, C$_1$-C$_8$haloalkoxy, mercapto, C$_1$-C$_8$alkylthio-, C$_1$-C$_8$haloalkylthio-, C$_1$-C$_8$alkylsulfinyl-, C$_1$-C$_8$haloalkylsulfinyl-, C$_1$-C$_8$alkylsulfonyl-, C$_1$-C$_8$haloalkylsulfonyl-, C$_1$-C$_8$alkylcarbonyl-, C$_1$-C$_8$alkoxycarbonyl-, aryl or aryl itself substituted by one to five substituents independently selected from halogen, C$_1$-C$_4$alkyl, C$_1$-C$_4$haloalkyl, C$_1$-C$_4$alkoxy, or C$_1$-C$_4$haloalkoxy, or heterocyclyl or heterocyclyl itself substituted by one to five substituents independently selected from halogen, C$_1$-C$_4$alkyl, C$_1$-C$_4$haloalkyl, C$_1$-C$_4$alkoxy, or C$_1$-C$_4$haloalkoxy;
each R$^7$ is independently halogen, cyano, nitro, C$_3$-C$_{10}$cycloalkyl, C$_3$-C$_{10}$halocycloalkyl, hydroxy, C$_1$-C$_8$alkoxy, C$_1$-C$_8$haloalkoxy, mercapto, C$_1$-C$_8$alkylthio-, C$_1$-C$_8$haloalkylthio-, C$_1$-C$_8$alkylsulfinyl-, C$_1$-C$_8$haloalkylsulfinyl-, C$_1$-C$_8$alkylsulfonyl-, or C$_1$-C$_8$haloalkylsulfonyl-; and
each R$^6$, R$^8$, R$^9$ and R$^{10}$ is independently halogen, cyano, nitro, C$_1$-C$_8$alkyl, C$_1$-C$_8$haloalkyl, C$_2$-C$_8$alkenyl, C$_2$-C$_8$haloalkenyl, C$_2$-C$_8$alkynyl, C$_2$-C$_8$haloalkynyl, hydroxy, C$_1$-C$_8$alkoxy, C$_1$-C$_8$haloalkoxy, mercapto, C$_1$-C$_8$alkylthio-, C$_1$-C$_8$haloalkylthio-, C$_1$-C$_8$alkylsulfinyl-, C$_1$-C$_8$haloalkylsulfinyl-, C$_1$-C$_8$alkylsulfonyl-, C$_1$-C$_8$haloalkylsulfonyl-, C$_1$-C$_8$alkylcarbonyl-, C$_1$-C$_8$alkoxycarbonyl-, aryl or aryl itself substituted by one to five substituents independently selected from halogen, C$_1$-C$_4$alkyl, C$_1$-C$_4$haloalkyl, C$_1$-C$_4$alkoxy, or C$_1$-C$_4$haloalkoxy, or heterocyclyl or heterocyclyl itself substituted by one to five substituents independently selected from halogen, C$_1$-C$_4$alkyl, C$_1$-C$_4$haloalkyl, C$_1$-C$_4$alkoxy, or C$_1$-C$_4$haloalkoxy; or a salt or N-oxide thereof. The preferred values of A$^1$, A$^2$, A$^3$, A$^4$, G$^1$, R$^1$, R$^2$, R$^3$, R$^4$, R$^6$, R$^7$, R$^8$, R$^9$, and R$^{10}$ are the same as set out above for a compound of formula (I). Preferably R$^5$ is halogen, C$_1$-C$_8$alkylthio-, C$_1$-C$_8$haloalkylthio-, C$_1$-C$_8$alkylsulfinyl-, C$_1$-C$_8$haloalkylsulfinyl-, C$_1$-C$_8$alkylsulfonyl-, or C$_1$-C$_8$haloalkylsulfonyl-, more preferably halogen, most preferably bromo.

Preferably, R$^2$ is thietanyl, oxo-thietanyl or dioxo-thietanyl, each optionally substituted by 1 to 5 R$^8$; Preferably, R$^2$ is thietanyl, oxo-thietanyl or dioxo-thietanyl, each linked via the 3-position.

Furthermore, the present invention therefore provides a compound of formula (I''')

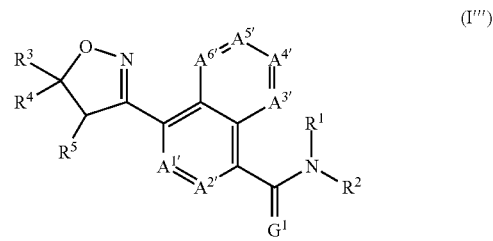

(I''')

wherein A$^{1'}$, A$^{2'}$, A$^{3'}$, A$^{4'}$, A$^{5'}$, and A$^{6'}$ are independently of each other C—H, C—R$^6$, or nitrogen; and wherein G, R$^1$, R$^2$, R$^3$, R$^4$, R$^5$ and R$^6$ are as defined for the compound of formula (I''').

In one embodiment the invention provides a compound of formula (I").

In one embodiment the invention provides a compound of formula (I'''). Furthermore, the present invention therefore provides a compound of formula (II") or a compound of formula (II''')

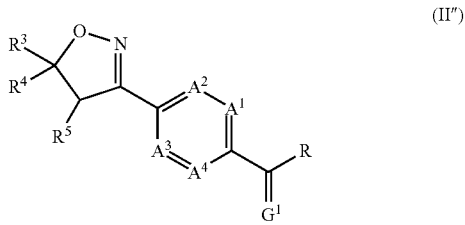

(II")

wherein A$^1$, A$^2$, A$^3$, A$^4$, R$^3$, R$^4$ and R$^5$ are as defined for a compound of formula (I"), G$^1$ is oxygen, and R is hydroxy, C$_1$-C$_6$alkoxy or halogen; or a salt or N-oxide thereof. The preferences for $A^1$, $A^2$, $A^3$, $A^4$, $R^3$, $R^4$ and $R^5$ are the same as the preferences set out for the corresponding substituents of a compound of formula (I'''). R is preferably chloro.

Furthermore, the present invention therefore provides a compound of formula (II''')

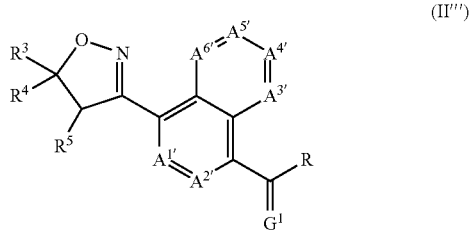

wherein $A^{1'}$, $A^{2'}$, $A^{3'}$, $A^{4'}$, $A^{5'}$, $A^{6'}$, $R^3$, $R^4$ and $R^5$ are as defined for a compound of formula (I'''), $G^1$ is oxygen, and R is hydroxy, $C_1$-$C_6$alkoxy or halogen; or a salt or N-oxide thereof. The preferences for $A^{1'}$, $A^{2'}$, $A^{3'}$, $A^{4'}$, $A^{5'}$, $A^{6'}$, $R^3$, $R^4$ and $R^5$ are the same as the preferences set out for the corresponding substituents of a compound of formula (I'''). R is preferably chloro.

In one embodiment the present invention provides a compound of formula (II'')

In one embodiment the present invention provides a compound of formula (II''')

Furthermore, the present invention provides a compound of formula ($I^a$) or ($I^b$):

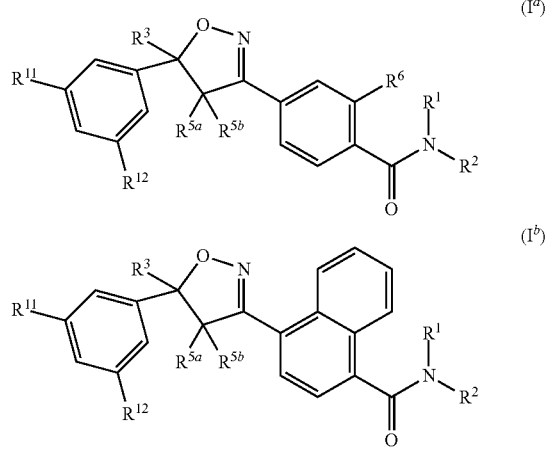

wherein
$R^1$ is hydrogen, methyl, or ethyl;
$R^2$ is thietanyl, oxo-thietanyl or dioxo-thietanyl, each linked to the nitrogen atom via the 3-position, and each optionally substituted by halogen, $C_1$-$C_4$ alkyl or $C_1$-$C_4$ haloalkyl;
$R^3$ is chlorodifluoromethyl or trifluoromethyl;
$R^{5a}$ is halogen, hydroxy, $C_1$-$C_4$ alkyl, $C_1$-$C_4$ haloalkyl, $C_1$-$C_4$ alkylthio, $C_1$-$C_4$ haloalkylthio, $C_1$-$C_4$ alkylsulfonyl, $C_1$-$C_4$ haloalkylsulfonyl, $C_1$-$C_4$ alkylsulfinyl, or $C_1$-$C_4$ haloalkylsulfinyl; and
$R^{5b}$ is hydrogen or halogen.
$R^{11}$ and $R^{12}$ are independently hydrogen, halogen $C_1$-$C_4$ alkyl or $C_1$-$C_4$ haloalkyl.
Preferably, the present invention provides a compound of formula ($I^a$) or ($I^b$) in which $R^1$ is hydrogen;
$R^2$ is thietanyl, oxo-thietanyl or dioxo-thietanyl, each linked via the 3-position, and each optionally substituted at the 3 position by methyl;
$R^3$ is trifluoromethyl;
$R^{5a}$ is halogen, hydroxyl, methyl, methylthio, methylsulfinyl or methylsulfonyl;
$R^{5a}$ is hydrogen or halogen;
$R^{11}$ and $R^{12}$ are independently fluorine, chlorine or bromine.

In one embodiment the invention provides a compound of formula ($I^a$).

In one embodiment the invention provides a compound of formula ($I^b$).

The compounds in Tables 1 to 9 below illustrate the compounds of the invention.

TABLE 1

Table 1 provides 50 compounds of formula (Ia) wherein $R^6$ is methyl, and $R^1$ and $R^2$ have the values listed in the table below.

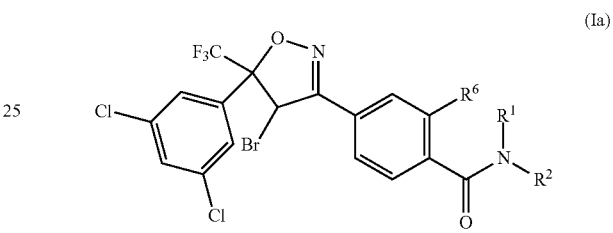

| Compound numbers | $R^1$ | $R^2$ |
|---|---|---|
| 1.01 | H | ethyl- |
| 1.02 | H | n-butyl- |
| 1.03 | H | but-2-yl- |
| 1.04 | H | 3-bromo-propyl- |
| 1.05 | H | 2,2,2-trifluoro-ethyl- |
| 1.06 | H | 3,3,3-trifluoro-propyl- |
| 1.07 | H | 2-methoxy-ethyl- |
| 1.08 | H | 1-methoxy-prop-2-yl- |
| 1.09 | H | phenyl-methyl- |
| 1.10 | H | 1-phenyl-eth-1-yl- |
| 1.11 | H | 2-phenyl-eth-1-yl- |
| 1.12 | H | (3-chloro-phenyl)-methyl- |
| 1.13 | H | (2-fluoro-phenyl)-methyl- |
| 1.14 | H | (4-methoxy-phenyl)-methyl- |
| 1.15 | H | (2-trifluoromethyl-phenyl)-methyl- |
| 1.16 | H | (2-trifluoromethoxy-phenyl)-methyl- |
| 1.17 | H | (pyrid-2-yl)-methyl- |
| 1.18 | H | (pyrid-3-yl)-methyl- |
| 1.19 | H | (2-chloro-pyrid-5-yl)-methyl- |
| 1.20 | H | (1-methyl-1H-imidazol-4-yl)-methyl- |
| 1.21 | H | (furan-2-yl)-methyl- |
| 1.22 | H | 2-(thiophen-2'-yl)-eth-1-yl- |
| 1.23 | H | 2-(indol-3'-yl)-eth-1-yl- |
| 1.24 | H | (1H-benzimidazol-2-yl)-methyl- |
| 1.25 | H | (oxetan-2-yl)-methyl- |
| 1.26 | H | (tetrahydrofuran-2-yl)-methyl- |
| 1.27 | H | 2-([1',3']dioxolan-2'-yl)-eth-1-yl- |
| 1.28 | H | 2-(morpholin-4'-yl)-eth-1-yl- |
| 1.29 | H | 2-(benzo[1',3']dioxol-5'-yl)-eth-1-yl- |
| 1.30 | H | (2,3-dihydro-benzo[1,4]dioxin-6-yl)-methyl- |
| 1.31 | H | cyclobutyl- |
| 1.32 | H | 2-methyl-cyclohex-1-yl- |
| 1.33 | H | 2-chloro-phenyl- |
| 1.34 | H | 3-fluoro-phenyl- |
| 1.35 | H | 2-methyl-phenyl- |
| 1.36 | H | 2-chloro-6-methyl-phenyl- |
| 1.37 | H | 2-trifluoromethyl-phenyl- |
| 1.38 | H | 2,4-dimethoxy-phenyl- |
| 1.39 | H | 3-methyl-pyrid-2-yl- |
| 1.40 | H | 1,3-dimethyl-1H-pyrazol-5-yl- |
| 1.41 | H | 4-methyl-thiazol-2-yl- |
| 1.42 | H | 5-methyl-thiadiazol-2-yl- |

TABLE 1-continued

Table 1 provides 50 compounds of formula (Ia) wherein $R^6$ is methyl, and $R^1$ and $R^2$ have the values listed in the table below.

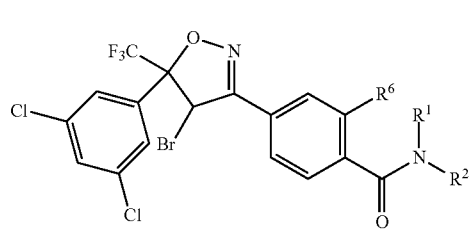

(Ia)

| Compound numbers | $R^1$ | $R^2$ |
|---|---|---|
| 1.43 | H | quinolin-2-yl- |
| 1.44 | H | quinolin-5-yl- |
| 1.45 | H | benzothiazol-6-yl- |
| 1.46 | H | 4-methyl-benzothiazol-2-yl- |
| 1.47 | H | thietan-3-yl- |
| 1.48 | H | 1-oxo-thietan-3-yl- |
| 1.49 | H | 1,1-dioxo-thietan-3-yl- |
| 1.50 | H | 3-methyl-thietan-3-yl- |

TABLE 2

Table 2 provides 50 compounds of formula (Ib) wherein $R^6$ is methyl, and $R^1$ and $R^2$ have the values listed in the table below.

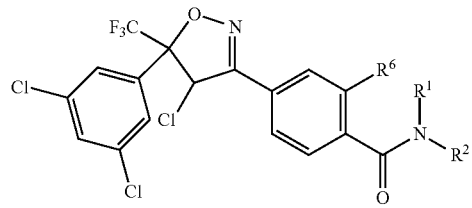

(Ib)

TABLE 3

Table 3 provides 50 compounds of formula (Ic) wherein $R^6$ is methyl, and $R^1$ and $R^2$ have the values listed in Table 1.

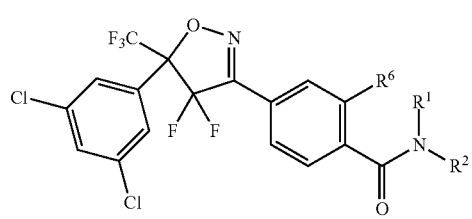

(Ic)

TABLE 4

Table 4 provides 50 compounds of formula (Ic) wherein $R^6$ is methyl, and $R^1$ and $R^2$ have the values listed in Table 1.

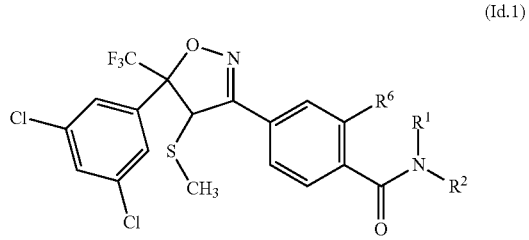

(Id.1)

TABLE 5

Table 5 provides 50 compounds of formula (Id.2) wherein $R^6$ is methyl, and $R^1$ and $R^2$ have the values listed in Table 1.

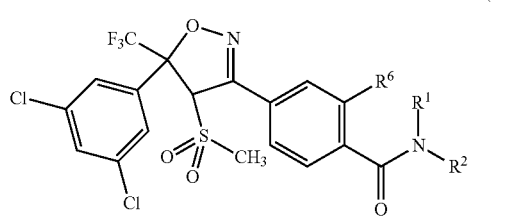

(Id.2)

TABLE 6

Table 6 provides 50 compounds of formula (Ie) wherein $R^6$ is methyl, and $R^1$ and $R^2$ have the values listed in Table 1.

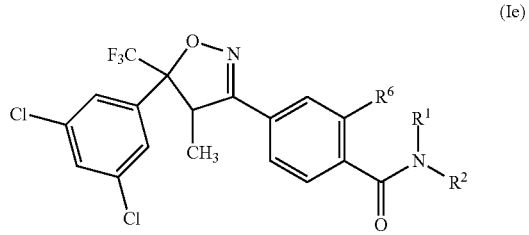

(Ie)

TABLE 7

Table 7 provides 50 compounds of formula (Ig) wherein $R^6$ is methyl, and $R^1$ and $R^2$ have the values listed in the table below.

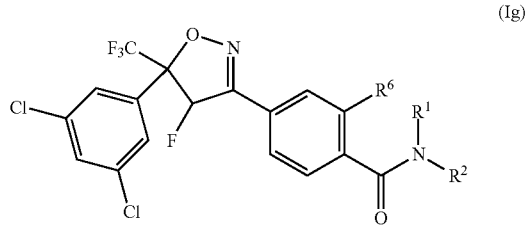

(Ig)

TABLE 8

Table 8 provides 50 compounds of formula (Ih) wherein $R^6$ is methyl, and $R^1$ and $R^2$ have the values listed in the table below.

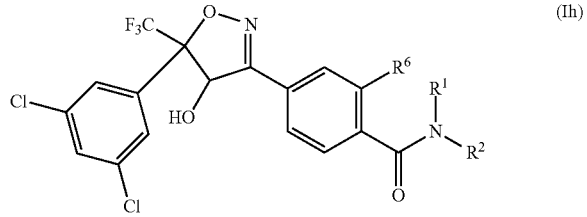

(Ih)

TABLE 9

Table 9 provides 50 compounds of formula (I'a) wherein $R^1$ and $R^2$ have the values listed in Table 1.

(I'a)

The compounds of formula (I) may be made by a variety of methods as shown in Schemes 1 to 8. The compounds of formula (I') may also be made by a variety of methods as shown in Schemes 1 to 8 except that the monocyclic ring is replaced with a bicyclic ring, as appropriate.

Scheme 1

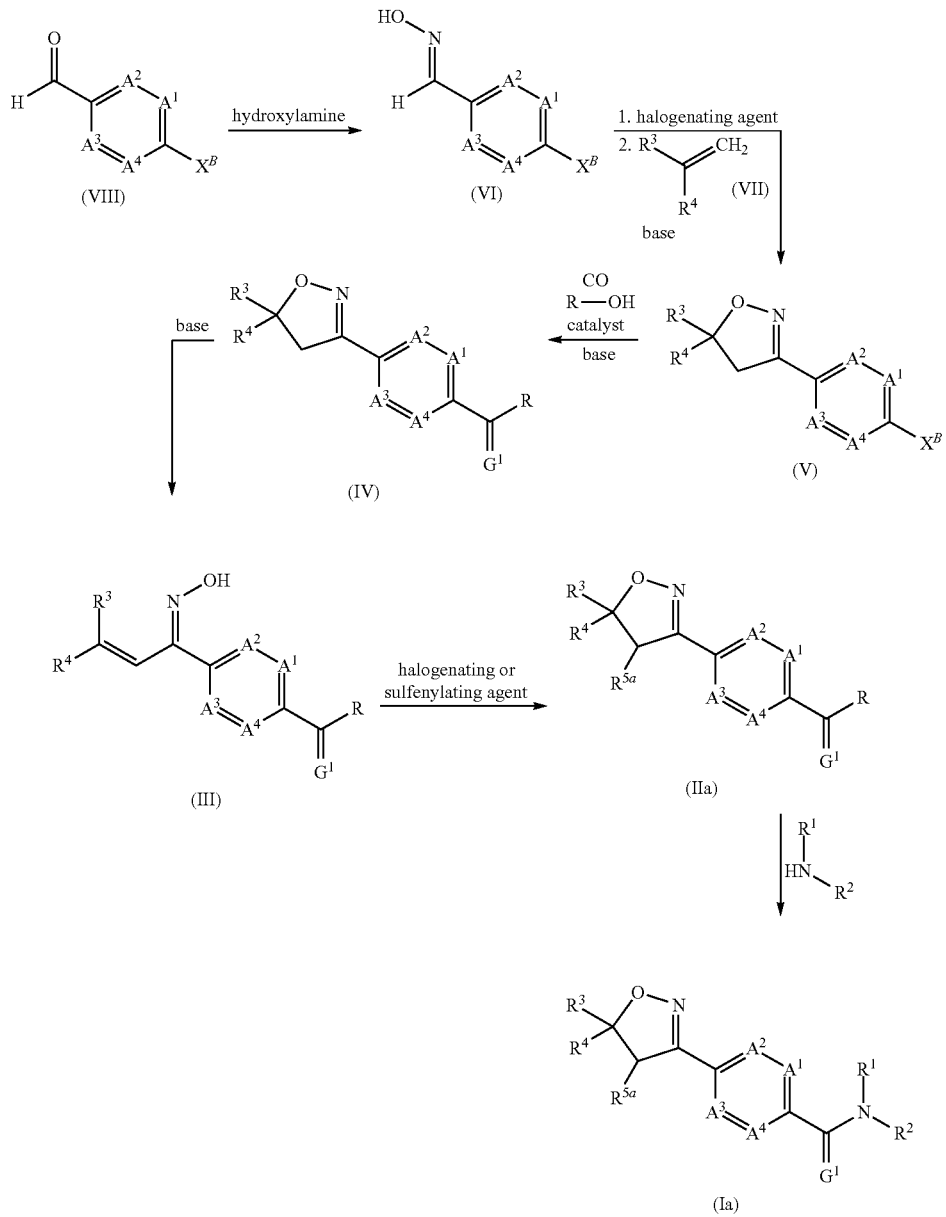

1) Compounds of formula (Ia), that is a compound of formula (I) wherein $R^{5a}$ is other than hydrogen and $R^{5b}$ is hydrogen, wherein $G^1$ is oxygen, can be prepared by reacting a compound of formula (IIa), that is a compound of formula (II) wherein $R^{5a}$ is other than hydrogen and $R^{5b}$ is hydrogen, wherein $G^1$ is oxygen and R is OH, $C_1$-$C_6$alkoxy or Cl, F or Br, with an amine of formula $HNR^1R^2$ as shown in Scheme 1. When R is OH such reactions are usually carried out in the presence of a coupling reagent, such as N,N'-dicyclohexyl-carbo-diimide ("DCC"), 1-ethyl-3-(3-dimethylaminopropyl) carbodiimide hydrochloride ("EDC") or bis(2-oxo-3-oxazo-lidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula $HNR^1R^2$ are commercially available or can be prepared using methods known to a person skilled in the art.

2) Acid halides of formula (IIa) wherein $G^1$ is oxygen and R is Cl, F or Br, may be made from carboxylic acids of formula (IIa) wherein $G^1$ is oxygen and R is OH, under standard conditions, such as treatment with thionyl chloride or oxalyl chloride. A preferred solvent is dichloromethane. The reaction is carried out at a temperature of from 0° C. to 100° C., preferably from 15° C. to 30° C., in particular at ambient temperature.

3) Carboxylic acids of formula (IIa) wherein $G^1$ is oxygen and R is OH, may be formed from esters of formula (IIa) wherein $G^1$ is oxygen and R is $C_1$-$C_6$alkoxy. It is known to a person skilled in the art that there are many methods for the hydrolysis of such esters depending on the nature of the alkoxy group. One widely used method to achieve such a transformation is the treatment of the ester with an alkali hydroxide, such as lithium hydroxide, sodium hydroxide or potassium hydroxide, in a solvent, such as ethanol or tetrahydrofuran, in the presence of water. Another transformation is the treatment of the ester with an acid, such as trifluoroacetic acid, in a solvent, such as dichloromethane, followed by addition of water. The reaction is carried out at a temperature of from 0° C. to 150° C., preferably from 15° C. to 100° C., in particular at 50° C.

4) Compounds of formula (IIa), that is a compound of formula (II) wherein $R^{5a}$ is other than hydrogen and $R^{5b}$ is hydrogen, wherein $G^1$ is oxygen and R is OH, $C_1$-$C_6$alkoxy or Cl, F or Br, can be made by reaction of a compound of formula (III) wherein $G^1$ is oxygen and R is OH, $C_1$-$C_6$alkoxy or Cl, F or Br, with a halogenating or sulfenylating agent, in the presence of a suitable solvent, for example a polar solvent, such as N,N-dimethylformamide. Suitable halogenating agents are, for example, 4-iodotoluene difluoride (CAS RN 371-11-9) or N-fluorobenzenesulfonimide ("NFSI"), N-chlorosuccinimide ("NCS"), N-bromo-succinimide ("NBS"), and N-iodosuccinimide ("NIS"), for making a compound where $R^{5a}$ is F, Cl, Br, or I, respectively. A suitable sulfenylating agent is, for example, methanesulfenyl chloride (MeS-Cl), S-methyl methanethiosulfonate ($MeSO_2$-SMe) or dimethyldisulfide (MeS-SMe), for making a compound where $R^{5a}$ is methylthio-. The reaction is carried out at a temperature of from −20° C. to +200° C., preferably from 0° C. to 150° C.

5) Compounds of formula (III) wherein $G^1$ is oxygen and R is OH, $C_1$-$C_6$alkoxy or Cl, F or Br, can be made by reaction of an isoxazoline of formula (IV) wherein $G^1$ is oxygen and R is OH, $C_1$-$C_6$alkoxy or Cl, F or Br, by treatment with base, such as lithium diisopropylamine ("LDA") in the presence of a solvent, such as tetrahydrofuran. The reaction is carried out at a temperature of from −150° C. to +30° C., preferably from −100° C. to 0° C.

6) Compounds of formula (IV) wherein $G^1$ is oxygen and R is $C_1$-$C_6$alkoxy, can be prepared by reacting a compound of formula (V) wherein $X^B$ is a leaving group, for example a halogen, such as bromo, with carbon monoxide and an alcohol of formula R—OH, such as ethanol, in the presence of a catalyst, such as bis(triphenylphosphine)palladium(II) dichloride, and a base, such as pyridine, triethylamine, 4-(dimethylamino)-pyridine ("DMAP") or diisopropylethylamine (Hunig's base). The reaction is carried out at a temperature of from 50° C. to 200° C., preferably from 100° C. to 150° C., in particular at 115° C. The reaction is carried out at a pressure of from 50 to 200 bar, preferably from 100 to 150 bar, in particular at 120 bar.

7) Compounds of formula (V) wherein $X^B$ is a leaving group as defined under 6), can be made by reaction of an oxime of formula (VI) wherein $X^B$ is a leaving group as defined under 6), and a vinyl compound of formula (VII) in a two step reaction. In the first step, the oxime of formula (VI) is reacted with a halogenating agent, for example a succinimide, such as N-chlorosuccinimide ("NCS"), in the presence of a suitable solvent, for example a polar solvent, such as N,N-dimethylformamide. The first step is carried out at a temperature of from 0° C. to 100° C., preferably from 15° C. to 30° C., in particular at ambient temperature.

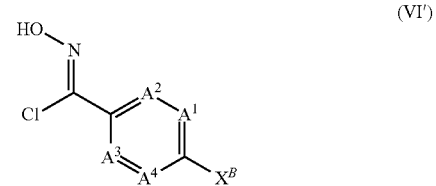

(VI')

In the second step, the chloro hydroxy imine intermediate of formula (VI') is reacted with the vinyl compound of formula (VII) in the presence of a base, for example an organic base, such as triethylamine, or an inorganic base, such as sodium hydrogen carbonate, in the presence of a suitable solvent, for example a polar solvent, such as N,N-dimethylformamide or isopropanol. It is possible to conduct these two steps separately and optionally to isolate the chloro hydroxy imine intermediate or more conveniently to conduct these two steps successively in one reaction vessel without isolation of the intermediate. The second step is carried out at a temperature of from 0° C. to 100° C., preferably from 15° C. to 30° C., in particular at ambient temperature. Vinyl compounds of formula (VII) are commercially available or can be made by methods known to a person skilled in the art.

8) Compounds of formula (VI) wherein $X^B$ is a leaving group as defined under 6), can be made by reaction of an aldehyde of formula (VIII) wherein $X^B$ is a leaving group as defined under 6), with a hydroxylamine, such as hydroxylamine hydrochloride. Such reactions are carried out optionally in the presence of a base, for example an organic base, such as triethylamine or sodium acetate, or an inorganic base, such as sodium hydrogen carbonate, optionally in the presence of a solvent, for example an alcohol, such as methanol or ethanol, or water, or mixtures thereof. The reaction is carried out at a temperature of from 0° C. to 100° C., preferably from 15° C. to 30° C., in particular at ambient temperature. Aldehydes of formula (VIII) are commercially available or can be made by methods known to a person skilled in the art.

9) Compounds of formula (Ia), that is a compound of formula (I) wherein $R^{5a}$ is other than hydrogen and $R^{5b}$ is hydrogen, wherein $G^1$ is sulfur, may be made by treatment of a compound of formula (IIa), that is a compound of formula (II) wherein $R^{5a}$ is other than hydrogen and $R^{5b}$ is hydrogen, wherein $G^1$ is oxygen and R is OH, $C_1$-$C_6$alkoxy or Cl, F or Br, with a thio-transfer reagent such as Lawesson's reagent or phosphorus pentasulfide prior to elaborating to compounds of formula (Ia), as described under 1).

10) Compounds of formula (I) with a sulfoxide group or a sulfone group can be made from a compound of formula (I) with a sulfide group (or sulfoxide group) in the corresponding position, by treatment with an oxidising reagent, such as potassium permanganate, 3-chloroperoxybenzoic acid ("MCPBA"), sodium periodate (optionally in the presence of ruthenium(II)oxide), hydrogen peroxide, oxone and sodium hypochlorite. One equivalent of oxidising reagent is required to convert a sulfide to a sulfoxide, or a sulfoxide to a sulfone. Two equivalents of oxidising reagent are required to convert a sulfide to a sulfone. Preferred solvents are tetrahydrofuran, dioxane, 1,2-dimethoxyethane, ethyl acetate, toluene, dichloromethane and water, or mixtures thereof. The reaction is optionally carried out in the presence of a base, for example a carbonate, such as sodium hydrogen carbonate. The reaction is carried out at a temperature of from 0° C. to 100° C., preferably from 15° C. to 30° C., in particular at ambient temperature.

methoxy or tert-butoxy, with a halogenating agent followed by a vinyl compound of formula (VII) and base in a two step reaction as described under 7). The intermediate of formula (XI') wherein $G^1$ is oxygen and R is $C_1$-$C_6$alkoxy, such as methoxy or tert-butoxy, can optionally be isolated.

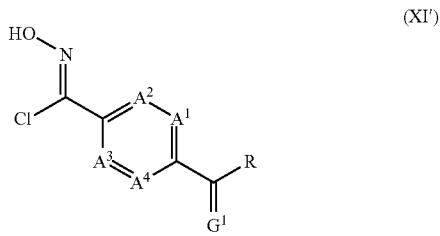

(XI')

12) Compounds of formula (XI) wherein $G^1$ is oxygen and R is $C_1$-$C_6$alkoxy, such as methoxy or tert-butoxy, can be made by reaction of an aldehyde of formula (XII) wherein $G^1$ is oxygen and R is $C_1$-$C_6$alkoxy, for example methoxy or tert-butoxy, with a hydroxylamine and optionally a base as described under 8).

13) Compounds of formula (XII) wherein $G^1$ is oxygen and R is $C_1$-$C_6$alkoxy, such as methoxy or tert-butoxy, can be prepared by reaction of a compound of formula (XIII) wherein $G^1$ is oxygen and R is $C_1$-$C_6$alkoxy, for example methoxy or tert-butoxy, and wherein $X^B$ is a leaving group as defined under 6), with a formylating agent, such as N,N-dimethylformamide. Such reactions are carried out in the presence of a base, for example a lithium base, such as n-butyl lithium, in the presence of a suitable solvent, for example a polar solvent, such as tetrahydrofuran or excess N,N-dimethylformamide. Compounds of formula (XIII) wherein $G^1$ is oxygen and R is $C_1$-$C_6$alkoxy, such as methoxy or tert-butoxy, are commercially available or can be made by methods known to a person skilled in the art.

Scheme 2

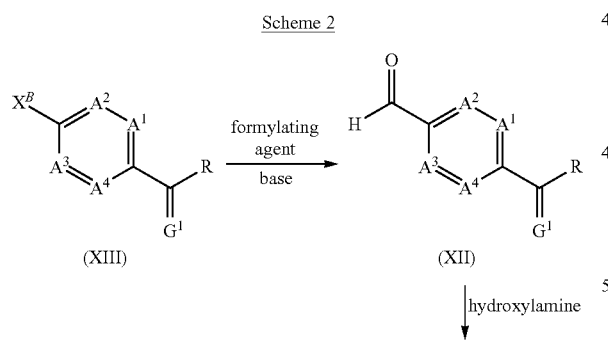

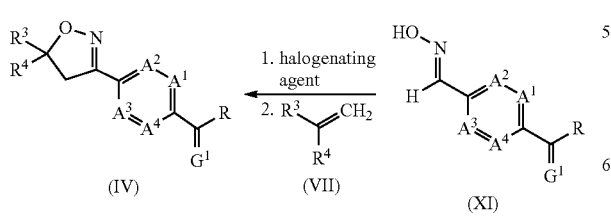

11) Alternatively, compounds of formula (IV) wherein $G^1$ is oxygen and R is $C_1$-$C_6$alkoxy, such as methoxy or tert-butoxy, can be prepared by reaction of an oxime of formula (XI) wherein $G^1$ is oxygen and R is $C_1$-$C_6$alkoxy, such as Scheme 3

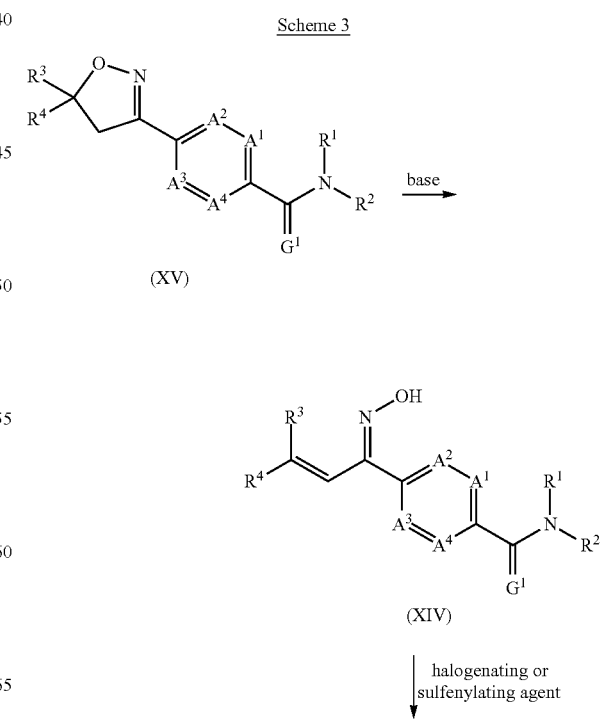

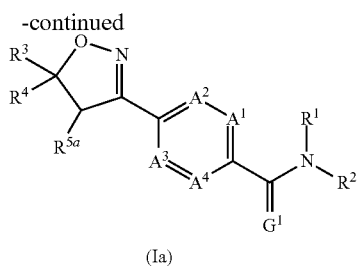

(Ia)

14) Alternatively, compounds of formula (Ia), that is a compound of formula (I) wherein $R^{5a}$ is other than hydrogen and $R^{5b}$ is hydrogen, wherein $G^1$ is oxygen, can be prepared by reaction of a compound of formula (XIV) wherein $G^1$ is oxygen, with a halogenating agent or sulfenylating agent as shown in Scheme 3 as described under 4).

15) Compounds of formula (XIV) wherein $G^1$ is oxygen, can be prepared by reaction of an isoxazoline of formula (XV) wherein $G^1$ is oxygen, with a base as described under 5). Compounds of formula (XV) wherein $G^1$ is oxygen, can be made by methods described, for example, in EP 1,731,512.

Scheme 4

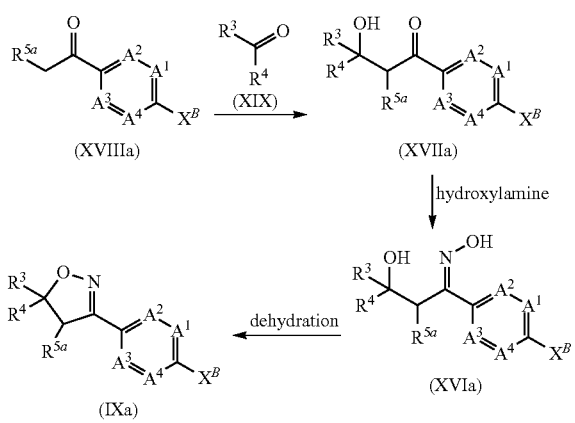

16) Compounds of formula (IXa), that is a compound of formula (IX) wherein $R^{5a}$ is other than hydrogen and $R^{5b}$ is hydrogen, wherein $X^B$ is a leaving group as defined under 6), can be prepared by cyclisation of a compound of formula (XVIa) wherein $X^B$ is a leaving group as defined under 6), as shown in Scheme 4. The cyclisation of a compound of formula (XVIa) can also be referred to as the dehydration of a compound of formula (XVIa). Such reactions are usually carried out in the presence of an acid, for example an inorganic acid, such as hydrochloric acid or sulfuric acid, or a sulfonic acid, such as methanesulfonic acid, optionally in a solvent, such as water, ethanol or tetrahydrofuran, or mixtures thereof. The reaction is carried out at a temperature of from 0° C. to 100° C., preferably from 40° C. to 80° C. Representative experimental conditions for this transformation are described in Synthetic Communications 2003, 23, 4163-4171. Alternatively, dehydration can be carried out using a dehydrating agent, such as phosphorus pentoxide, in a solvent, such as chloroform, at a temperature of from −20° C. to 50°, preferably at 0° C., as described in Journal of Heterocyclic Chemistry 1990, 27, 275. Alternatively, cyclisation can be carried out under Mitsunobu conditions involving treatment of a compound of formula (XVIa) with a phosphine, such as triphenylphosphine, and an azodicarboxylate reagent, such as diethyl azodicarboxylate, diisopropyl azodicarboxylate or dicyclohexyl azodicarboxylate, in a solvent, such as tetrahydrofuran, at a temperature of from 0° C. to 80° C., preferably from 0° C. to ambient temperature.

17) Compounds of formula (XVIa) wherein $X^B$ is a leaving group as defined under 6), can be made by reaction of a β-hydroxy ketone of formula (XVIIa) wherein $X^B$ is a leaving group as defined under 6), with a hydroxylamine and optionally a base as described under 8).

18) Compounds of formula (XVIIa) wherein $X^B$ is a leaving group as defined under 6), can be made by aldol-type reaction of a substituted methyl ketone of formula (XVIIIa) wherein $X^B$ is a leaving group as defined under 6), with a ketone of formula (XIX). Such reactions are usually carried out in the presence of a base, such as sodium hydride, lithium hydride, lithium diisopropylamide or lithium hexamethyldisilazide, in a solvent, such as tetrahydrofuran, at a temperature of from −78° C. to +100° C., preferably from 0° C. to +80° C. Alternatively, the reaction can be performed using a Lewis acid, such as titanium tetrachloride, and an amine, such as triethylamine, diisopropylethylamine, tetramethylethylenediamine ("TMEDA") or tributylamine, in a solvent, such as dichloromethane, at a temperature of from −78° C. to ambient temperature, preferably at −78° C. Representative conditions for such a transformation are given in Tetrahedron Letters 1997, 38, 8727-8730. Ketones of formula (XIX) are commercially available or can be made by methods known to a person skilled in the art. Substituted methyl ketones of formula (XVIIIa) are known in the literature or can be prepared, for example, from the corresponding unsubstituted ketone.

Scheme 5

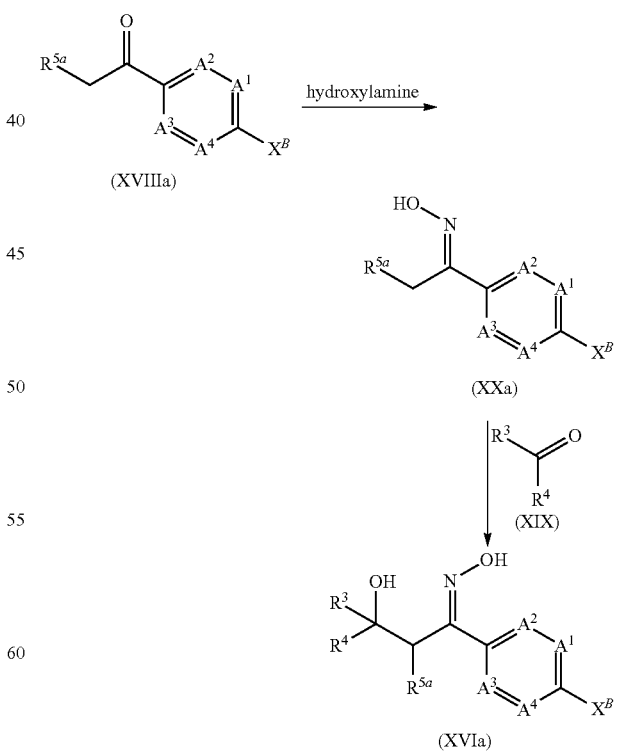

20) Alternatively, compounds of formula (XVIa) wherein $X^B$ is a leaving group as defined under 6), can be prepared by reacting a substituted methyl oxime of formula (XXa) wherein $X^B$ is a leaving group as defined under 6), with a ketone of formula (XIX) in an aldol-type reaction as shown in Scheme 5. Such reactions are usually carried out by treating the substituted methyl oxime of formula (XXa) with a base, such as n-butyl lithium, lithium diisopropylamide or lithium hexamethyldisilazide, in a solvent, such as tetrahydrofuran, at a temperature of from −78° C. to ambient temperature, preferably from −20° C. to 0° C., followed by addition of the ketone of formula (XIX) at a temperature of from −78° C. to 0° C., preferably at 0° C. Representative conditions for such a transformation can be found in Synthetic Communications, 2003, 23, 4163-4171.

21) Compounds of formula (XXa) wherein $X^B$ is a leaving group as defined under 6), can be made by reaction of a substituted methyl ketone of formula (XVIIIa) wherein $X^B$ is a leaving group as defined under 6), with a hydroxylamine and optionally a base as described under 8).

Scheme 6

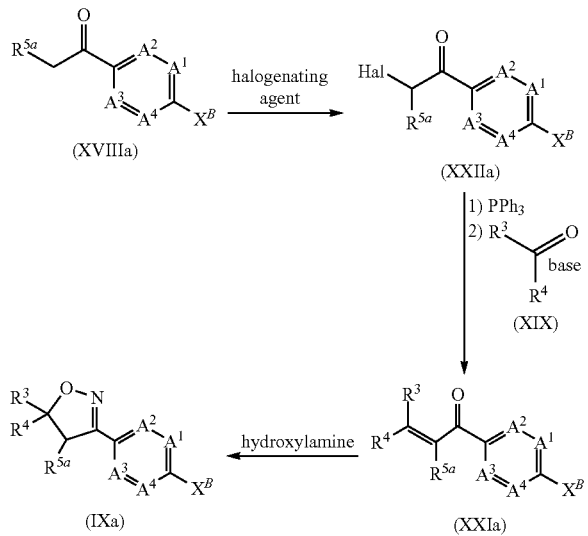

22) Alternatively, compounds of formula (IXa), that is a compound of formula (IX) wherein $R^{5a}$ is other than hydrogen and $R^{5b}$ is hydrogen, wherein $X^B$ is a leaving group as defined under 6), can be obtained by reacting an unsaturated ketone of formula (XXIa) wherein $X^B$ is a leaving group as defined under 6), with a hydroxylamine, such as hydroxylamine hydrochloride, as shown on Scheme 6. Such reactions can be performed optionally in the presence of a base, such as sodium hydroxide or potassium hydroxide, in a solvent, such as methanol, ethanol or water, or mixtures thereof, at a temperature of from 0° C. to 100° C., preferably from ambient temperature to 80° C. Such conditions are described, for example, in J. Indian Chemical Society 1988, 65(9), 640-2. Such reactions may optionally lead to intermediates of formula (XXIa') wherein $X^B$ is a leaving group as defined under 6)

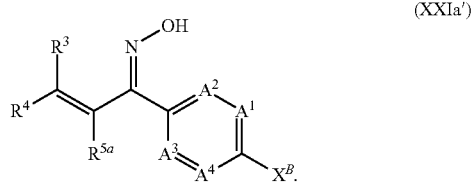

Such intermediates can be converted into compounds of formula (IXa) in the presence of an acid, such as hydrochloric acid or acetic acid, or mixtures thereof, or a base, such as sodium methoxide, optionally in a solvent, such as methanol or diethyl ether, at a temperature of from 0° C. to 100° C. Representative procedures for this reaction are described in Eur. J. Org. Chem. 2002, p 1919.

23) Compounds of formula (XXIa) wherein $X^B$ is a leaving group as defined under 6), can be obtained by various methods. For example, they can be prepared by reacting in a first step a compound of formula (XXIIa) wherein $X^B$ is a leaving group as defined under 6) and Hal is a halogen, such as bromo or chloro, with a phosphine, such as triphenylphosphine. Such reactions are usually performed in a solvent, such as toluene, at a temperature of from ambient temperature to 150° C., preferably from 80° C. to 120° C. In a second step, the intermediate is treated with a ketone of formula (XIX) and a base, such as n-butyl lithium or triethylamine, in a solvent, such as tetrahydrofuran, at a temperature of from −78° C. to +100° C., preferably from ambient temperature to +80° C. Such conditions are described, for example, in Journal of Organic Chemistry 2006, 71(9), 3545-3550.

24) Compounds of formula (XXIIa) wherein $X^B$ is a leaving group as defined under 6) and Hal is a halogen, such as bromo or chloro, can be prepared by reacting a substituted methyl ketone of formula (XVIIIa) wherein $X^B$ is a leaving group as defined under 6), with a halogenating agent, such as bromine or chlorine, in a solvent, such as acetic acid, at a temperature of from 0° C. to 50° C., preferably from ambient temperature to 40° C.

Scheme 7

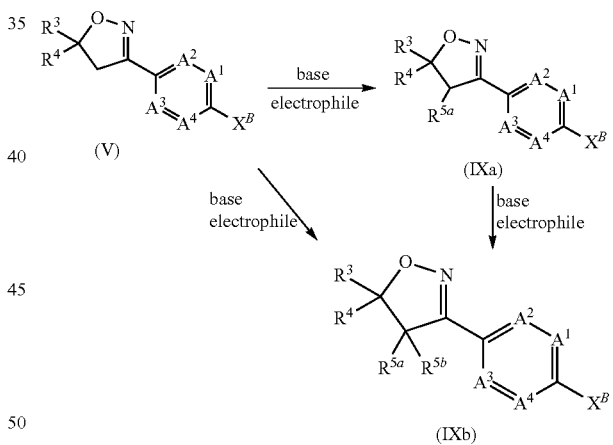

25) Compounds of formula (IXa), that is a compound of formula (IX) wherein $R^{5a}$ is other than hydrogen and $R^{5b}$ is hydrogen, wherein $X^B$ is a leaving group as defined under 6), can be made by treatment of a compound of formula (V) wherein $X^B$ is a leaving group as defined under 6), with base, such as lithium diisopropylamine ("LDA"), followed by the addition of an electrophile, for example a halogenating agent, a sulfenylating agent or an alkylating agent, in the presence of a suitable solvent, such as tetrahydrofuran, as shown in Scheme 7. Suitable halogenating agents are, for example, those mentioned under 6). Suitable sulfenylating agents are, for example, those mentioned under 6). Suitable alkylating agents are, for example, alkyl halides, such as methyl iodide (Me-I), for making a compound where $R^{5a}$ is $C_1$-$C_8$alkyl, in particular methyl, and cyanating agents such as cyanogen bromide, 1-cyanobenzotriazole, phenyl cyanate ("PhOCN") or tosyl cyanide for making a compound where $R^{5a}$ is cyano. Suitable hydroxylating agents are, for example, oxaziridines (for instance, N-sulfonyl oxaziridines) or oxodiperoxymolybdenum(pyridine)-(hexamethyl-phosphoric triamide) ("MoOPH") for making a compound where $R^{5a}$ is hydroxy. The reaction is carried out at a temperature of from −120° C. to +30° C., preferably from −100° C. to 0° C.

26) Compounds of formula (IXb), that is a compound of formula (IX) wherein both $R^{5a}$ and $R^{5b}$ are other than hydrogen, wherein $X^B$ is a leaving group as defined under 6), can be made by treatment of a compound of formula (V) wherein $X^B$ is a leaving group as defined under 6), with two equivalents of base and two equivalents of electrophile as defined under 25) applied simultaneously or successively. Where $R^{5a}$ and $R^{5b}$ are the same it is preferred to carry out the reactions simultaneously, without isolation of the intermediate. Where $R^{5a}$ and $R^{5b}$ are different it is preferred to carry out the reactions successively, optionally isolating the intermediate. Alternatively, a compound of formula (IXb), could be made from a compound of formula (IXa) which itself was obtained, for example, using a method shown in Scheme 4 or Scheme 6.

could be made from a compound of formula (IIa) which itself was obtained, for example, using a method shown in Scheme 1 or Scheme 2.

29) Alternatively, compounds of formula (I) can be prepared using the methods described on Scheme 1 and 2 wherein the vinyl compound of formula (VII) is replaced by an alkene compound of formula (VII'):

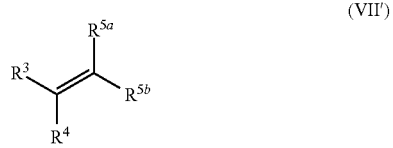

(VII')

wherein $R^{5a}$ and $R^{5b}$ are not both hydrogen.

WO 2009/080250 discloses the preparation of compounds containing a group

Scheme 8

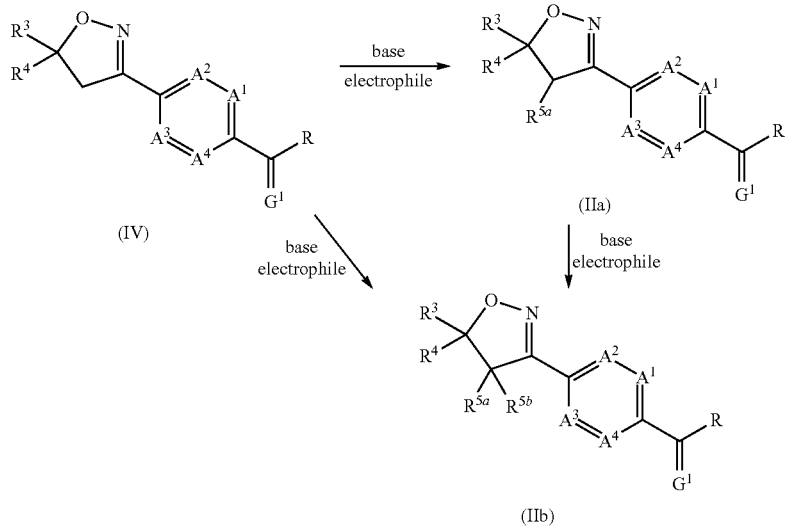

27) Alternatively, compounds of formula (IIa) that is a compound of formula (II) wherein $R^{5a}$ is other than hydrogen and $R^{5b}$ is hydrogen, wherein $G^1$ is oxygen and R is $C_1$-$C_6$alkoxy, such as methoxy or tert-butoxy, can be prepared by reaction of an isoxazoline of formula (IV) wherein $G^1$ is oxygen and R is $C_1$-$C_6$alkoxy, such as methoxy tert-butoxy, with a base and an electrophile as defined under 25) as shown in Scheme 8.

28) Compounds of formula (IIb), that is a compound of formula (II) wherein both $R^{5a}$ and $R^{5b}$ are other than hydrogen, can be made by treatment of a compound of formula (IV) with two equivalents of base and two equivalents of electrophile as defined under 25) applied simultaneously or successively. Where $R^{5a}$ and $R^{5b}$ are the same it is preferred to carry out the reactions simultaneously, without isolation of the intermediate. Where $R^{5a}$ and $R^{5b}$ are different it is preferred to carry out the reactions successively, optionally isolating the intermediate. Alternatively, a compound of formula (IIb),

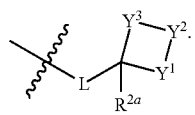

The compounds of formula (I) or formula (I') can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fiber products), horticulture and animal husbandry, companion animals, forestry and the storage of products of vegetable origin (such as fruit, grain and timber);

those pests associated with the damage of man-made structures and the transmission of diseases of man and animals; and also nuisance pests (such as flies).

Examples of pest species which may be controlled by the compounds of formula (I) or formula (I') include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus*, and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I) or formula (I'), or a composition containing a compound of formula (I) or formula (I'), to a pest, a locus of pest, preferably a plant, or to a plant susceptible to attack by a pest, The compounds of formula (I) or formula (I') are preferably used against insects, acarines or nematodes.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) or formula (I') as an insecticide, acaricide, nematicide or molluscicide to a pest, a locus of pest, or to a plant susceptible to attack by a pest, a compound of formula (I) or formula (I') is usually formulated into a composition which includes, in addition to the compound of formula (I) or formula (I'), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I) or formula (I'). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) or formula (I') is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) or formula (I') and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I) or formula (I').

Dustable powders (DP) may be prepared by mixing a compound of formula (I) or formula (I') with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) or formula (I') with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) or formula (I') with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) or formula (I') and one or more powdered solid diluents or carriers, or from pre-formed blank granules by absorbing a compound of formula (I) or formula (I') (or a solution thereof, in a suitable agent) in a porous granular material (such as pumice, attapulgite clays, fuller's earth, kieselguhr, diatomaceous earths or ground corn cobs) or by adsorbing a compound of formula (I) or formula (I') (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) or formula (I') in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) or formula (I') in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) or formula (I') either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) or formula (I') is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I) or formula (I'). SCs may be prepared by ball or bead milling the solid compound of formula (I) or formula (I') in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) or formula (I') may be dry milled and added to water, containing agents hereinbefore described, to produce the desired end product.

Aerosol formulations comprise a compound of formula (I) or formula (I') and a suitable propellant (for example n-butane). A compound of formula (I) or formula (I') may also be dissolved or dispersed in a suitable medium (for example water or a water miscible liquid, such as n-propanol) to provide compositions for use in non-pressurized, hand-actuated spray pumps.

A compound of formula (I) or formula (I') may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) or formula (I') and, optionally, a carrier or diluent therefor. The polymeric shell may be produced by either an interfacial polycondensation reaction or by a coacervation procedure. The compositions may provide for controlled release of the compound of formula (I) or formula (I') and they may be used for seed treatment. A compound of formula (I) or formula (I') may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I) or formula (I')). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I) or formula (I')).

A compound of formula (I) or formula (I') may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) or formula (I') may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) or formula (I') may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) or formula (I') (for example 0.0001 to 10%, by weight) depending upon the purpose for which they are to be used.

A compound of formula (I) or formula (I') may be used in mixtures with fertilizers (for example nitrogen-, potassium- or phosphorus-containing fertilizers). Suitable formulation types include granules of fertilizer. The mixtures preferably contain up to 25% by weight of the compound of formula (I) or formula (I').

The invention therefore also provides a fertilizer composition comprising a fertilizer and a compound of formula (I) or formula (I').

The compositions of this invention may contain other compounds having biological activity, for example micronutrients or compounds having fungicidal activity or which possess plant growth regulating, herbicidal, insecticidal, nematicidal or acaricidal activity.

The compound of formula (I) or formula (I') may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I) or formula (I'); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad, azadirachtin or spinetoram;

h) Hormones or pheromones;

i) Organochlorine compounds, such as endosulfan (in particular alpha-endosulfan), benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds, such as imidacloprid, thiacloprid, acetamiprid, nitenpyram, dinotefuran, thiamethoxam, clothianidin, nithiazine or flonicamid;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine;

r) Spirotetramat, spirodiclofen or spiromesifen;

s) Diamides, such as flubendiamide, chlorantraniliprole (Rynaxypyr®) or cyantraniliprole;

t) Sulfoxaflor; or u) Metaflumizone.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethyl-benzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) or formula (I') may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

PREPARATION EXAMPLES

The following abbreviations were used in this section: s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; M.p.=melting point; RT=retention time, $[M+H]^+$ =molecular mass of the molecular cation, $[M-H]^-$ =molecular mass of the molecular anion.

The following LC-MS methods were used to characterize the compounds:

| Method B | |
|---|---|
| MS | ZMD Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 150, desolvation temperature (° C.) 320, cone gas flow (L/Hr) 50, desolvation gas flow (L/Hr) 400, mass range: 150 to 800 Da. |
| LC | Alliance 2795 LC HPLC from Waters: quaternary pump, heated column compartment and diode-array detector. Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile. |

| Time (min) | A % | B % | Flow (ml/min) |
|---|---|---|---|
| 0.0 | 80 | 20 | 1.7 |
| 5.0 | 0.0 | 100 | 1.7 |
| 5.6 | 0.0 | 100 | 1.7 |
| 6.0 | 80 | 20 | 1.7 |

| Method E | |
|---|---|
| MS | ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da. |
| LC | 1100er Series HPLC from Agilent: quaternary pump, heated column compartment and diode-array detector. Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile. |

| Time (min) | A % | B % | Flow (ml/min) |
|---|---|---|---|
| 0.0 | 80 | 20 | 1.7 |
| 2.5 | 0.0 | 100 | 1.7 |
| 2.8 | 0.0 | 100 | 1.7 |
| 2.9 | 80 | 20 | 1.7 |

| Method F | |
|---|---|
| MS | ZQ Mass Spectrometer from Waters (single quadrupole mass spectrometer), ionization method: electrospray, polarity: negative ionization, capillary (kV) 3.00, cone (V) 45.00, source temperature (° C.) 100, desolvation temperature (° C.) 250, cone gas flow (L/Hr) 50, desolvation gas flow (L/Hr) 400, mass range: 150 to 1000 Da. |
| LC | HP 1100 HPLC from Agilent: solvent degasser, binary pump, heated column compartment and diode-array detector. Column: Phenomenex Gemini C18, length (mm) 30, internal diameter (mm) 3, particle size (μm) 3, temperature (° C.) 60, DAD wavelength range (nm): 200 to 500, solvent gradient: A = 0.05% v/v formic acid in water and B = 0.04% v/v formic acid in acetonitrile/methanol (4:1). |

-continued

Method F

| Time (min) | A % | B % | Flow (ml/min) |
|---|---|---|---|
| 0.0 | 95 | 5.0 | 1.7 |
| 2.0 | 0.0 | 100 | 1.7 |
| 2.8 | 0.0 | 100 | 1.7 |
| 2.9 | 95 | 5.0 | 1.7 |
| 3.1 | 95 | 5 | 1.7 |

1. Reactions Which Are Covered by Scheme 1

Example 1.1

Preparation of 4-bromo-3-methyl-benzaldehyde

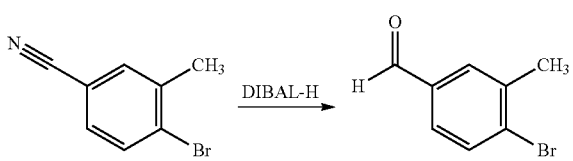

A solution of 4-bromo-3-methyl-benzonitrile (commercially available) (500 mg) in dichloromethane (7.5 ml) was added at 0° C. to a solution of diisobutylaluminium hydride ("DIBAL-H") (2.6 ml) in hexanes (1M). The reaction mixture was stirred at 0° C. for 2 hours. The reaction mixture was poured on a mixture of ice (10 g) and aqueous hydrobromic acid (6M) (10 ml). The mixture was allowed to warm to ambient temperature and then extracted twice with dichloromethane. The combined organic phases were washed with water, dried over sodium sulfate, and concentrated to give 4-bromo-3-methyl-benzaldehyde (0.419 g) as a colorless oil. $^1$H-NMR (400 MHz, CDCl$_3$): 9.95 (s, 1H), 7.72 (m, 2H), 7.55 (d, 1H), 2.50 (s, 3H) ppm.

Example 1.2

Preparation of 4-bromo-3-methyl-benzaldehyde oxime

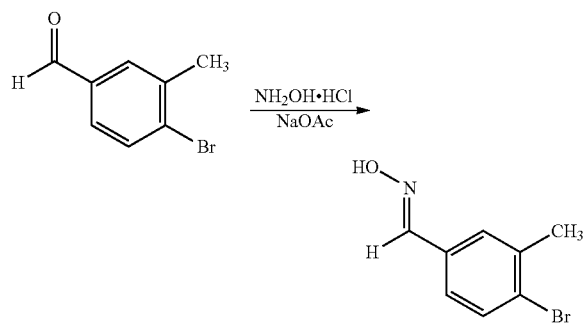

To a solution of 4-bromo-3-methyl-benzaldehyde (4.3 g) (Example 1.1) in ethanol (50 ml), were added at ambient temperature hydroxylamine hydrochloride (1.75 g), sodium acetate (2.07 g) and water (15 ml). The reaction mixture was stirred at ambient temperature for 3 hours. The reaction mixture was concentrated and the residue was partitioned between ethyl acetate and aqueous sodium hydroxide (2M). The phases were separated and the organic phase was washed with brine, dried over sodium sulfate, and concentrated. The residue was purified by chromatography on silica gel (eluent: cyclohexane/ethyl acetate 4:1) to give 4-bromo-3-methyl-benzaldehyde oxime (3.65 g) as a white solid. $^1$H-NMR (400 MHz, CDCl$_3$): 8.05 (s, 1H), 7.50 (m, 2H), 7.25 (d, 1H), 2.40 (s, 3H) ppm.

Example 1.3

Preparation of 3-(4-bromo-3-methyl-phenyl)-5-(3,5-dichloro-phenyl)-5-trifluoromethyl-4,5-dihydro-isoxazole

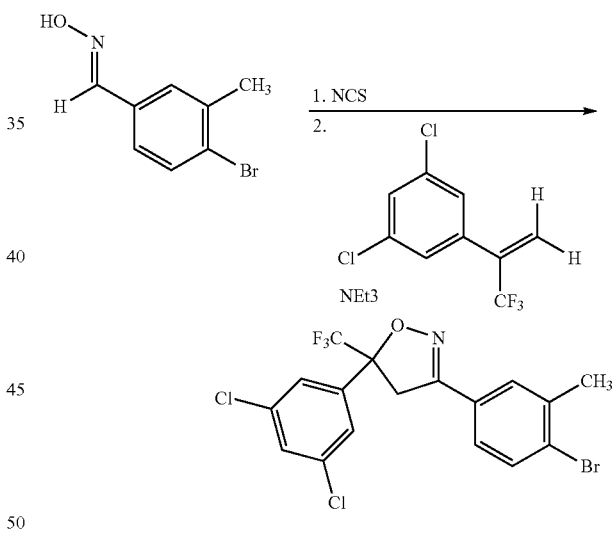

4-Bromo-3-methyl-benzaldehyde oxime (1.3 g) (Example 1.2) and N-chloro-succinimide ("NCS") (1.8 g) were dissolved in N,N-dimethylformamide (15 ml). The reaction mixture was stirred at ambient temperature for 90 minutes. A solution of 1,3-dichloro-5-(1-trifluoromethyl-vinyl)-benzene (1.3 g) (prepared according to WO 2005/085216) and triethylamine (1.9 ml) in N,N-dimethylformamide (15 ml) was added and the reaction mixture was stirred at ambient temperature for 18 hours. The reaction mixture was diluted with water and ethyl acetate and the phases were separated. The organic phase was washed twice with water and the aqueous phases were extracted twice with ethyl acetate. The combined organic phases were dried over sodium sulfate and concentrated. The residue was purified by chromatography on silica gel (eluent: cyclohexane/dichloromethane 4:1) to give 3-(4-bromo-3-methyl-phenyl)-5-(3,5-dichloro-phenyl)-5-trifluoromethyl-4,5-dihydro-isoxazole (1.57 g). ¹H-NMR (400 MHz, CDCl₃): 7.40 (m, 6H), 4.05 (d, 1H), 3.65 (d, 1H), 2.40 (s, 3H) ppm.

Example 1.4

Preparation of 4-[5-(3,5-dichloro-phenyl)-5-trifluoromethyl-4,5-dihydro-isoxazol-3-yl]-2-methyl-benzoic acid ethyl ester

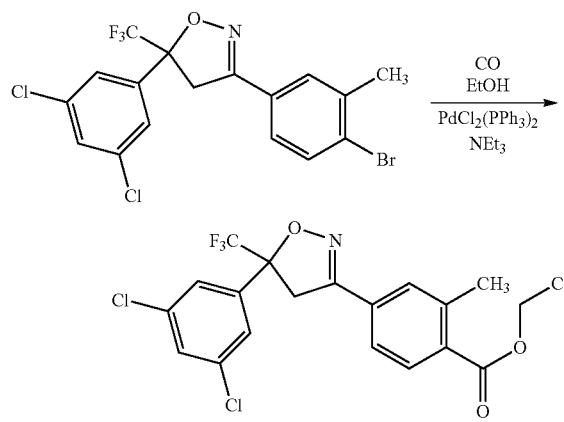

Triethylamine (1.2 ml) was added at ambient temperature to a solution of 3-(4-bromo-3-methyl-phenyl)-5-(3,5-dichloro-phenyl)-5-trifluoromethyl-4,5-dihydro-isoxazole (1.2 g) (Example 1.3) in ethanol (45 ml). Bis(triphenylphosphine)palladium(II)dichloride ("PdCl₂(PPh₃)₂") (0.185 g) was added and the reaction mixture was stirred in a pressure reactor in an atmosphere of carbon monoxide (120 bar) at 115° C. for 8 hours. The reaction mixture was cooled to ambient temperature, filtered over Celite® and concentrated. The residue was purified by preparative HPLC to give 4-[5-(3,5-dichloro-phenyl)-5-trifluoro-methyl-4,5-dihydro-isoxazol-3-yl]-2-methyl-benzoic acid ethyl ester (0.85 g) as a yellow oil. ¹H-NMR (CDCl₃, 400 MHz): 7.95 (d, 1H), 7.55 (m, 4H), 7.45 (s, 1H), 4.40 (q, 2H), 4.10 (d, 1H), 3.7 (d, 1H), 2.60 (s, 3H), 1.40 (t, 3H) ppm.

Example 1.5

Preparation of 4-[3-(3,5-dichloro-phenyl)-4,4,4-trifluoro-1-hydroxyimino-but-2-enyl]-2-methyl-benzoic acid ethyl ester

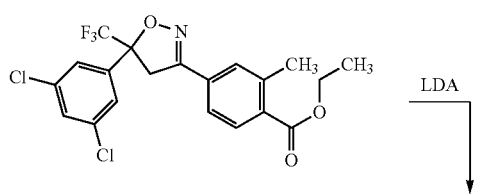

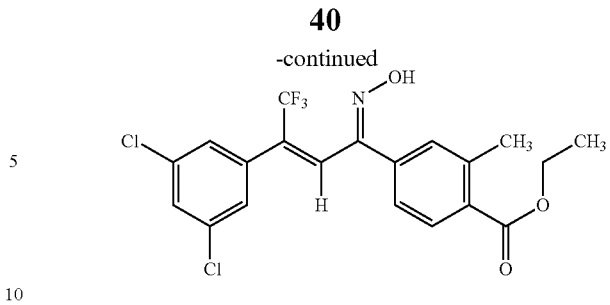

4-[3-(3,5-Dichloro-phenyl)-4,4,4-trifluoro-1-hydroxyimino-but-2-enyl]-2-methyl-benzoic acid ethyl ester was obtained from 4-[5-(3,5-dichloro-phenyl)-5-trifluoromethyl-4,5-dihydro-isoxazol-3-yl]-2-methyl-benzoic acid ethyl ester (Example 1.4) in a procedure similar to that described in Example 2.1. ¹H-NMR (CDCl₃, 400 MHz): 7.86-7.44 (m, 6H), 6.78 (s, 1H), 4.38 (q, 2H), 2.64 (s, 3H), 1.40 (t, 3H) ppm.

Similarly, 4-[3-(3,5-dichloro-phenyl)-4,4,4-trifluoro-1-hydroxyimino-but-2-enyl]-naphthalene-1-carboxylic acid methyl ester was obtained from 4-[5-(3,5-dichloro-phenyl)-5-trifluoromethyl-4,5-dihydro-isoxazol-3-yl]-naphthalene-1-carboxylic acid methyl ester (prepared according to WO 2007/079162). ¹H-NMR (CDCl₃, 300 MHz): 8.93 (d, 1H), 8.35 (d, 1H), 8.18-8.14 (m, 2H), 7.70-7.55 (m, 3H), 7.52 (d, 1H), 7.44 (t, 1H), 7.36 (t, 1H), 7.13 (s, 1H), 4.15 (s, 3H) ppm.

Example 1.6

Preparation of 4-[4-bromo-5-(3,5-dichloro-phenyl)-5-trifluoromethyl-4,5-dihydro-isoxazol-3-yl]-2-methyl-benzoic acid ethyl ester

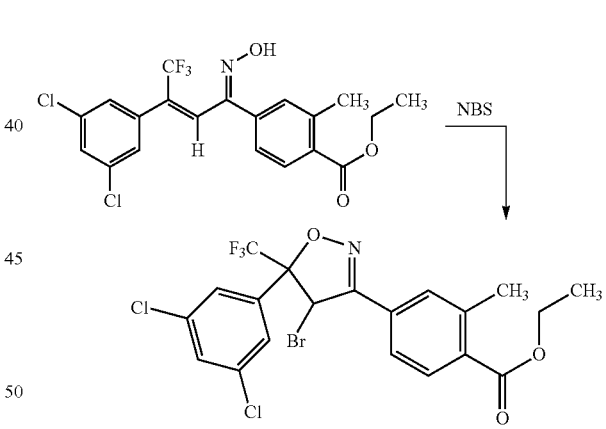

4-[4-Bromo-5-(3,5-dichloro-phenyl)-5-trifluoromethyl-4,5-dihydro-isoxazol-3-yl]-2-methyl-benzoic acid ethyl ester was obtained from 4-[3-(3,5-dichloro-phenyl)-4,4,4-trifluoro-1-hydroxyimino-but-2-enyl]-2-methyl-benzoic acid ethyl ester (Example 1.5) in a procedure similar to that described in Example 2.2. ¹H-NMR (CDCl₃, 400 MHz): 8.02-7.47 (m, 6H), 5.87 (s, 1H), 4.39 (q, 2H), 2.66 (s, 3H), 1.42 (t, 3H) ppm.

Similarly, 4-[4-bromo-5-(3,5-dichloro-phenyl)-5-trifluoromethyl-4,5-dihydro-isoxazol-3-yl]-naphthalene-1-carboxylic acid methyl ester was obtained from 4-[3-(3,5-dichloro-phenyl)-4,4,4-trifluoro-1-hydroxyimino-but-2-enyl]-naphthalene-1-carboxylic acid methyl ester (Example 1.5). ¹H-NMR (CDCl₃, 300 MHz): 8.96-8.88 (m, 1H), 8.48-

8.42 (m, 1H), 8.18 (d, 1H), 7.74-7.64 (m, 3H), 7.56 (m, 2H), 7.49 (t, 1H), 6.07 (s, 1H), 4.03 (s, 3H) ppm.

Example 1.7

Preparation of 4-[4-bromo-5-(3,5-dichloro-phenyl)-5-trifluoromethyl-4,5-dihydroisoxazol-3-yl]-2-methyl-benzoic acid

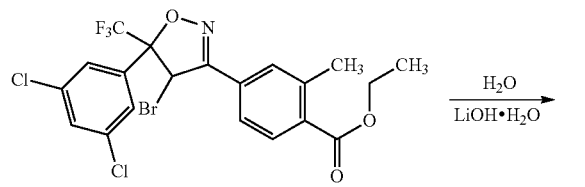

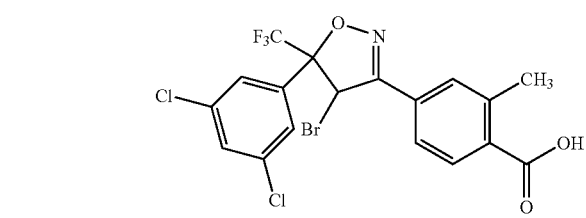

A mixture of 4-[4-bromo-5-(3,5-dichloro-phenyl)-5-trifluoromethyl-4,5-dihydro-isoxazol-3-yl]-2-methyl-benzoic acid ethyl ester (0.71 g, 1.35 mmol) (Example 1.6), lithium hydroxide monohydrate (0.17 g, 4 mmol), methanol (25 ml) and water (5 ml) was stirred at ambient temperature for 60 hours. The mixture was concentrated and the residue dissolved in water. The solution was acidified by addition of aqueous hydrochloric acid (1N). The precipitate was isolated by filtration and dried under vacuum to afford 4-[4-bromo-5-(3,5-dichloro-phenyl)-5-trifluoromethyl-4,5-dihydroisoxazol-3-yl]-2-methyl-benzoic acid (0.59 g, 88% yield) as a white powder. $^{1}$H-NMR (CDCl$_3$, 400 MHz): 8.05-7.45 (m, 6H), 5.87 (s, 1H), 2.65 (s, 3H) ppm.

The benzoic acid methyl esters obtained in Example 1.6, Example 3.1, Example 3.2 and Example 3.3 were converted into the corresponding benzoic acids using the method described here.

Example 1.8

General Method for Preparing the Compounds of the Invention in Parallel

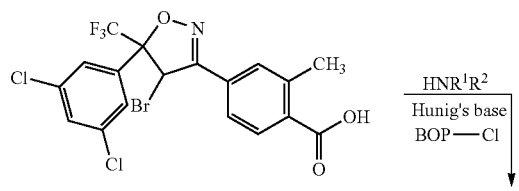

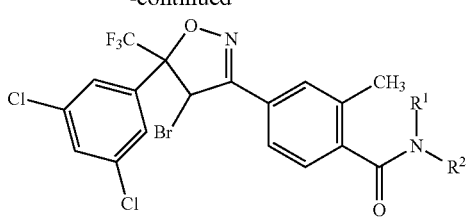

This general method was used to prepare a number of compounds (Compound Nos. A1 to A24 of Table A) in parallel. To a solution of the carboxylic acid (30 µmol), such as 4-[4-bromo-5-(3,5-dichloro-phenyl)-5-trifluoromethyl-4,5-dihydro-isoxazol-3-yl]-2-methyl-benzoic acid (Example 1.7) in the case of Compound No. A1 of Table A, in N,N-dimethyl-acetamide ("DMA") (0.4 ml) was added a solution amine (30 µmol), such as n-butyl amine in the case of Compound No. A1 of Table A, in N,N-dimethylacetamide ("DMA") (0.145 ml) followed by diisopropylethylamine (Hunig's Base) (0.02 ml, 100 µmol) and a solution of bis(2-oxo-3-oxazolidinyl)phosphonic chloride ("BOP-Cl") (15.3 mg) in N,N-dimethyl-acetamide ("DMA") (0.2 ml). The reaction mixture was stirred for 16 hours at 80° C. Then the mixture was diluted with acetonitrile (0.6 ml) and a sample was used for the LC-MS analysis. The remaining mixture was further diluted with acetonitrile/dimethylformamide (4:1, 0.8 ml) and purified by HPLC to give the desired compound.

Similarly, Compound Nos. B1-B23 of Table B were made from 4-[4-chloro-5-(3,5-dichloro-phenyl)-5-trifluoromethyl-4,5-dihydro-isoxazol-3-yl]-2-methyl-benzoic acid (Example 1.7). Similarly, Compound Nos. F1-F22 of Table F were made from 4-[4-bromo-5-(3,5-dichloro-phenyl)-5-trifluoromethyl-4,5-dihydro-isoxazol-3-yl]-naphthalene-1-carboxylic acid (Example 1.7). Similarly, Compound Nos. G1-G4 of Table G were made from 4-[5-(3,5-dichloro-phenyl)-4-fluoro-5-trifluoromethyl-4,5-dihydro-isoxazol-3-yl]-2-methyl-benzoic acid (Example 1.11). Similarly, Compound Nos. H1-H4 of Table H were made from 4-[5-(3,5-dichloro-phenyl)-4-hydroxy-5-trifluoromethyl-4,5-dihydro-isoxazol-3-yl]-2-methyl-benzoic acid (Example 1.11).

Example 1.9

Preparation of 4-[5-(3,5-dichloro-phenyl)-4,4-difluoro-5-trifluoromethyl-4,5-dihydro-isoxazol-3-yl]-2-methyl-N-pyridin-2-ylmethyl-benzamide (Compound No. C1 of Table C)

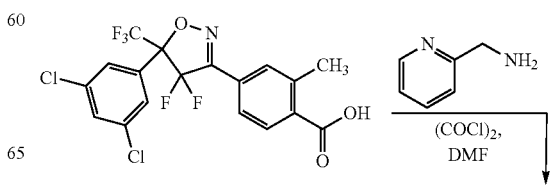

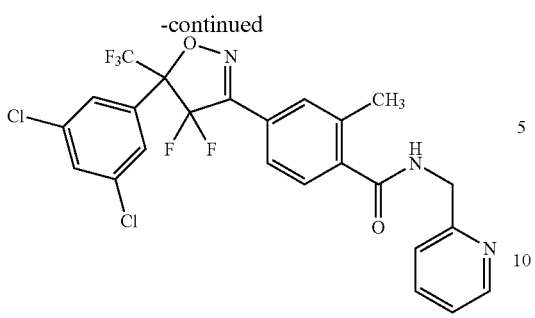

To a solution of 4-[5-(3,5-dichloro-phenyl)-4,4-difluoro-5-methyl-4,5-dihydro-isoxazol-3-yl]-2-methyl-benzoic acid (Example 1.7) (0.024 g) in dichloromethane (2 ml) was added oxalyl chloride (0.01 ml). After addition of N,N-dimethylformamide ("DMF") (2 drops) the reaction mixture was stirred at ambient temperature for 15 minutes. To this reaction mixture was slowly added 2-picolylamine (0.1 ml). The reaction mixture was stirred at ambient temperature for 2 hours. The reaction mixture was diluted with water and dichloromethane and the phases were separated. The organic phase was washed twice with water, dried over sodium sulfate and concentrated. The residue was purified by chromatography on silica gel (eluent: heptane/ethyl acetate 1:0 to 0:1) to give Compound No. C1 of Table C (20 mg) as a white foam. $^1$H-NMR (CDCl$_3$, 400 MHz): 8.52 (bs, 1H), 7.72-7.67 (m, 2H), 7.59-7.51 (m, 4H), 7.33 (d, 1H), 7.25-7.21 (m, 2H), 4.75 (2H, d), 2.52 (s, 3H) ppm.

Similarly, N-butyl-4-[5-(3,5-dichloro-phenyl)-4-methyl-sulfanyl-5-trifluoromethyl-4,5-dihydro-isoxazol-3-yl]-2-methyl-benzamide (Compound No. D1 of Table D) was obtained from 4-[5-(3,5-dichloro-phenyl)-4-methylsulfanyl-5-trifluoromethyl-4,5-dihydro-isoxazol-3-yl]-2-methyl-benzoic acid methyl ester (Example 1.7) and n-butylamine. $^1$H-NMR (CDCl$_3$, 400 MHz): 7.75-7.71 (m, 2H), 7.56-7.40 (m, 4H), 5.75-5.72 (m, 1H), 4.95 (s, 1H), 3.45 (q, 2H), 2.48 (s, 3H), 1.64-1.33 (m, 4H), 1.42 (s, 3H), 0.96 (t, 3H) ppm.

Similarly, N-butyl-4-[5-(3,5-dichloro-phenyl)-4-methyl-sulfonyl-5-trifluoromethyl-4,5-dihydro-isoxazol-3-yl]-2-methyl-benzamide (Compound No. D2 of Table D) was obtained from 4-[5-(3,5-dichloro-phenyl)-4-methylsulfonyl-5-trifluoromethyl-4,5-dihydro-isoxazol-3-yl]-2-methyl-benzoic acid methyl ester (Example 1.7) and n-butylamine. $^1$H-NMR (CDCl$_3$, 400 MHz): 7.67-7.43 (m, 6H), 5.79-5.73 (m, 1H), 5.26 (s, 1H), 3.45 (q, 2H), 2.49 (3, 3H), 2.47 (s, 3H), 1.63-1.38 (m, 4H), 0.96 (t, 3H) ppm.

Similarly, 4-[5-(3,5-dichloro-phenyl)-4-methylsulfanyl-5-trifluoromethyl-4,5-dihydro-isoxazol-3-yl]-2-methyl-N-thietan-3-yl-benzamide (Compound No. D3 of Table D) was obtained from 4-[5-(3,5-dichloro-phenyl)-4-methylsulfanyl-5-trifluoromethyl-4,5-dihydro-isoxazol-3-yl]-2-methyl-benzoic acid methyl ester (Example 1.7) and thietan-3-yl-amine. $^1$H-NMR (CDCl$_3$, 400 MHz): 7.76-7.73 (m, 2H), 7.56-7.42 (m, 4H), 6.22-6.20 (m, 1H), 5.45-5.39 (m, 1H), 4.95 (s, 1H), 3.51-3.33 (m, 4H), 2.48 (s, 3H), 1.42 (s, 3H) ppm.

Similarly, 4-[5-(3,5-dichloro-phenyl)-4-methylsulfonyl-5-trifluoromethyl-4,5-dihydro-isoxazol-3-yl]-2-methyl-N-thietan-3-yl-benzamide (Compound No. D4 of Table D) was obtained from 4-[5-(3,5-dichloro-phenyl)-4-methylsulfonyl-5-trifluoromethyl-4,5-dihydro-isoxazol-3-yl]-2-methyl-benzoic acid methyl ester (Example 1.7) and thietan-3-yl-amine. $^1$H-NMR (CDCl$_3$, 400 MHz): 7.69-7.61 (m, 4H), 7.53 (t, 1H), 7.45 (d, 1H), 6.26 (d, 1H), 5.44-5.38 (m, 1H), 5.26 (m, 1H), 3.51-3.46 (m, 2H), 3.39-3.35 (m, 2H), 2.49 (s, 3H), 2.47 (s, 3H) ppm.

Similarly, N-butyl-4-[5-(3,5-dichloro-phenyl)-4-methyl-5-trifluoromethyl-4,5-dihydro-isoxazol-3-yl]-2-methyl-benzamide (Compound No. E1 of Table E) was obtained from 4-[5-(3,5-dichloro-phenyl)-4-methyl-5-trifluoromethyl-4,5-dihydro-isoxazol-3-yl]-2-methyl-benzoic acid methyl ester (Example 1.7) and n-butylamine. $^1$H-NMR (CDCl$_3$, 400 MHz): 7.54-7.38 (m, 6H), 5.72-5.67 (m, 1H), 4.19-4.02 (m, 1H), 3.47-3.41 (m, 2H), 2.48 and 2.45 (s, 3H), 1.63-1.37 (m, 4H), 0.98-0.91 (m, 6H) ppm.

Similarly, 4-[5-(3,5-dichloro-phenyl)-4-methyl-5-trifluoromethyl-4,5-dihydro-isoxazol-3-yl]-2-methyl-N-thietan-3-yl-benzamide (Compound No. E2 of Table E) was obtained from 4-[5-(3,5-dichloro-phenyl)-4-methyl-5-trifluoromethyl-4,5-dihydro-isoxazol-3-yl]-2-methyl-benzoic acid methyl ester (Example 1.7) and thietan-3-yl-amine. $^1$H-NMR (CDCl$_3$, 400 MHz): 7.53-7.38 (m, 6H), 6.34-6.26 (m, 1H), 5.45-5.36 (m, 1H), 4.19-4.03 (m, 1H), 3.49-3.34 (m, 4H), 2.45 and 2.42 (s, 3H), 1.56-1.54 and 0.92-0.90 (m, 3H) ppm.

Example 1.10

Preparation of 4-[4-bromo-5-(3,5-dichloro-phenyl)-5-trifluoromethyl-4,5-dihydro-isoxazol-3-yl]-2-methyl-N-(1-oxo-thietan-3-yl)-benzamide, isomer A and isomer B (Compound Nos. A25 and A26 of Table A)

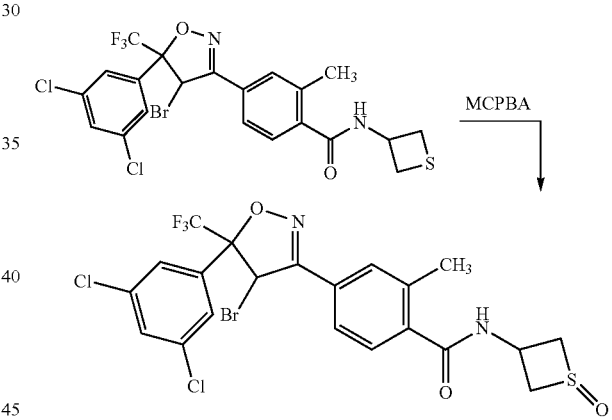

To a solution of 4-[4-bromo-5-(3,5-dichloro-phenyl)-5-trifluoromethyl-4,5-dihydro-isoxazol-3-yl]-2-methyl-N-thietan-3-yl-benzamide (145 mg) (Example A22) in dichloromethane (8 ml) was added a solution of sodium hydrogen carbonate (128 mg) in water (4 ml). A solution of 3-chloroperoxybenzoic acid ("MCPBA") (48 mg) in dichloromethane (1 ml) was added dropwise. The reaction mixture was stirred at ambient temperature for 4 hours. Dichloromethane was evaporated and the residue partitioned between aqueous sodium carbonate (1M) and ethyl acetate. The phases were separated and the aqueous phase extracted twice with ethyl acetate. The combined organic phases were dried over sodium sulfate and concentrated. The residue was purified by preparative HPLC to give Compound No. A25 of Table A (101 mg) and Compound No. A26 of Table A (17 mg) as colorless solids.

Compound No. A25 of Table A. $^1$H-NMR (CDCl$_3$, 400 MHz): 7.70-7.40 (m, 6H), 6.55 (d, 1H), 5.85 (s, 1H), 4.70 (m, 1H), 4.15 (m, 2H), 3.25 (m, 2H), 2.50 (s, 3H) ppm.

Compound No. A26 of Table A. $^{1}$H-NMR (CDCl$_3$, 400 MHz): 7.75-7.40 (m, 6H), 6.58 (d, 1H), 5.90 (s, 1H), 5.20 (m, 1H), 3.75 (m, 2H), 3.50 (m, 2H), 2.50 (s, 3H) ppm.

Example 1.11

Preparation of 4-[5-(3,5-dichloro-phenyl)-4-fluoro-5-trifluoromethyl-4,5-dihydro-isoxazol-3-yl]-2-methyl-benzoic acid

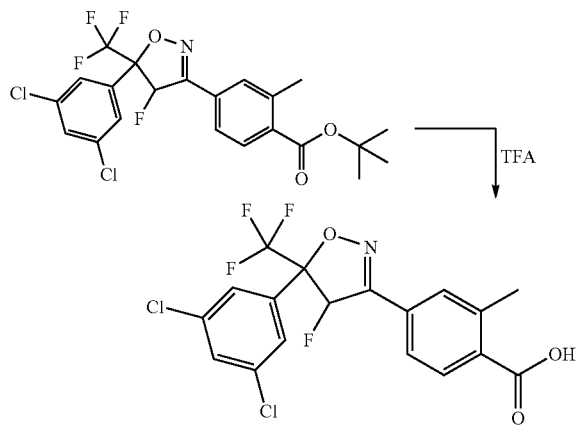

To a solution of 4-[5-(3,5-dichloro-phenyl)-4-fluoro-5-trifluoromethyl-4,5-dihydro-isoxazol-3-yl]-2-methyl-benzoic acid tert-butyl ester (Example 3.4) (310 mg) in dichloromethane (3.1 ml) was added trifluoroacetic acid ("TFA") (0.62 ml). The reaction mixture was stirred at ambient temperature for 16 hours. The reaction mixture was concentrated and the residue taken up in dichloromethane and water. The phases were separated and the organic layer was washed successively with water and brine, dried over magnesium sulfate, and concentrated to give a 1:1 mixture of the diastereoisomers of 4-[5-(3,5-dichloro-phenyl)-4-fluoro-5-trifluoromethyl-4,5-dihydro-isoxazol-3-yl]-2-methyl-benzoic acid (255 mg) as a white solid. $^{1}$H-NMR (CDCl$_3$, 400 MHz): 8.13 (2×d, 1H), 7.68 (m, 2H), 7.60 (2×s, 1H), 7.52 (2×s, 1H), 7.48 (m, 1H), 6.48 and 6.35 (2×d, 1H), 2.70 and 2.68 (2×s, 3H).

Similarly, 4-[5-(3,5-dichloro-phenyl)-4-hydroxy-5-trifluoromethyl-4,5-dihydro-isoxazol-3-yl]-2-methyl-benzoic acid was obtained from 4-[5-(3,5-dichloro-phenyl)-4-hydroxy-5-trifluoromethyl-4,5-dihydro-isoxazol-3-yl]-2-methyl-benzoic acid tert-butyl ester (Example 3.5). M.p. 215-217° C. $^{1}$H-NMR (CDCl$_3$, 400 MHz): 7.98 (d, 1H), 7.72 (s, 1H), 7.69 (s, 1H), 7.52 (s, 2H), 7.40 (s, 1H), 5.76 (s, 1H), 2.61 (s, 3H).

2. Reactions Which Are Covered by Scheme 3

Example 2.1

Preparation of N-butyl-4-[3-(3,5-dichloro-phenyl)-4,4,4-trifluoro-1-hydroxy-imino-but-2-enyl]-2-methyl-benzamide

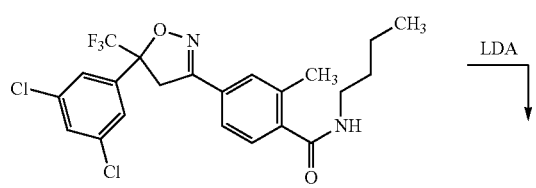

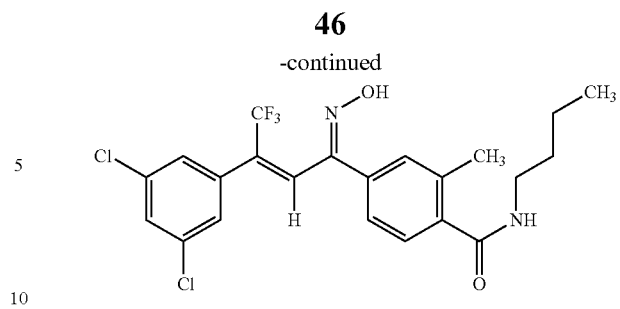

To a solution of N-butyl-4-[5-(3,5-dichloro-phenyl)-5-trifluoromethyl-4,5-dihydro-isoxazol-3-yl]-2-methyl-benzamide (made as described in EP 1,731,512) (1670 mg, 4.13 mmol) and N,N-diisopropylamine (880 mg, 8.69 mmol) in dry tetrahydrofuran (10 ml) was added n-butyl lithium ("n-BuLi") (1.55M in hexane) (5.6 ml, 8.69 mmol) at −90° C. The reaction mixture was allowed to warm to 0° C. over a period of 2 hours and quenched by addition of aqueous ammonium chloride (saturated). The mixture was extracted several times with diethyl ether. The combined organic extracts were dried over magnesium sulfate and concentrated. The residue was purified by chromatography on silica gel (eluent: hexane/ethyl acetate 2:1) to give N-butyl-4-[3-(3,5-dichloro-phenyl)-4,4,4-trifluoro-1-hydroxyimino-but-2-enyl]-2-methyl-benzamide (1180 mg, 70% yield) as a yellow resin. $^{1}$H-NMR (CDCl$_3$, 300 MHz): 8.52 (bs, 1H), 7.45-7.36 (m, 6H), 6.75 (s, 1H), 5.81 (m, 1H), 3.46-3.43 (m, 2H), 2.47 (s, 3H), 1.54-1.39 (m, 4H), 0.97 (t, 3H) ppm.

Example 2.2

Alternative preparation of 4-[4-bromo-5-(3,5-dichloro-phenyl)-5-trifluoromethyl-4,5-dihydro-isoxazol-3-yl]-N-butyl-2-methyl-benzamide (Compound No. A1 of Table A)

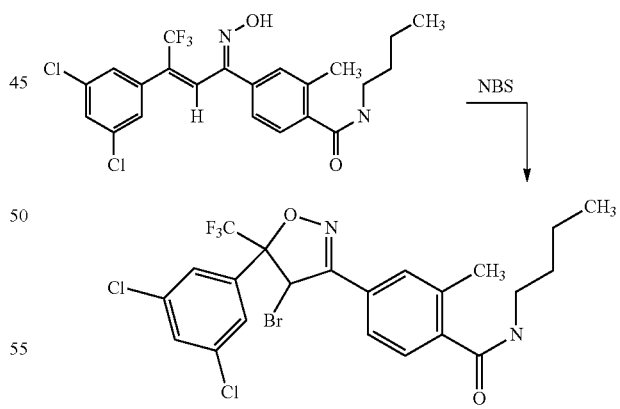

N-Butyl-4-[3-(3,5-dichloro-phenyl)-4,4,4-trifluoro-1-hydroxyimino-but-2-enyl]-2-methyl-benzamide (Example 3.1) (380 mg, 0.94 mmol) and N-bromosuccinimide (200 mg, 1.12 mmol) were heated in N,N-dimethylformamide (2 ml) at 120° C. for 7 minutes. The reaction mixture was allowed to cool to ambient temperature and then extracted with diethyl ether. The combined organic extracts were dried over magnesium sulfate and concentrated. The residue was purified by chromatography on silica gel (eluent: hexane/ethyl acetate 4:1) to give Compound No. A1 of Table A (210 mg, 40% yield) as a solid foam.

3. Reactions Which Are Covered by Scheme 8

Example 3.1

Preparation of 4-[5-(3,5-dichloro-phenyl)-4-methyl-5-trifluoromethyl-4,5-dihydro-isoxazol-3-yl]-2-methyl-benzoic acid methyl ester

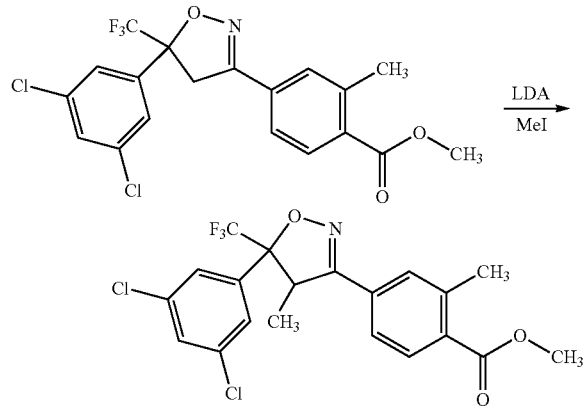

To a solution of N,N-diisopropylamine (0.24 ml) in dry tetrahydrofuran (8 ml) stirred under argon at 0° C., was added n-butyl lithium ("n-BuLi") (2.5 M in hexane) (0.74 ml). The solution was stirred at 0° C. for 30 minutes then was cooled to −85° C. To this solution was added a solution of 4-[5-(3,5-dichloro-phenyl)-5-trifluoromethyl-4,5-dihydro-isoxazol-3-yl]-2-methyl-benzoic acid methyl ester (made as described in EP 1,731,512) (500 mg) in dry tetrahydrofuran (3 ml). The reaction mixture was stirred at −85° C. until deprotonation was completed as monitored by thin layer chromatography. Then, to this solution was added methyl iodide (0.14 ml) and the reaction mixture was stirred at −85° C. for 1 hour. More methyl iodide (0.08 ml) was added and the reaction mixture was stirred at −85° C. for a further 30 minutes. Then the reaction was quenched by addition of aqueous ammonium chloride (saturated) at −85° C. The mixture allowed to warm to ambient temperature and was then extracted with dichloromethane. The combined organic extracts were dried over magnesium sulfate and concentrated. The residue was purified by chromatography on silica gel (eluent: heptane/ethyl acetate 85:15) to give 4-[5-(3,5-dichloro-phenyl)-4-methyl-5-trifluoromethyl-4,5-dihydro-isoxazol-3-yl]-2-methyl-benzoic acid methyl ester (290 mg) as a white foam. $^{1}$H-NMR (CDCl$_3$, 400 MHz): 7.98-7.92 (m, 1H), 7.58-7.38 (m, 5H) 4.22-4.05 (m, 1H), 3.90 (s, 3H), 3.89 (s, 3H), 2.63 (s, 3H), 2.60 (s, 3H), 1.58-1.56 (m, 3H), 0.94-0.92 (m, 3H) ppm.

Similarly, 4-[5-(3,5-dichloro-phenyl)-4-chloro-5-trifluoromethyl-4,5-dihydro-isoxazol-3-yl]-2-methyl-benzoic acid methyl ester was obtained using two equivalents of N-chlorosuccinimide ("NCS") as an electrophile.

Similarly, 4-[5-(3,5-dichloro-phenyl)-4-methylsulfanyl-5-trifluoromethyl-4,5-dihydro-isoxazol-3-yl]-2-methyl-benzoic acid methyl ester was obtained using 1.7 equivalents of S-methyl methanethiosulfonate as an electrophile. $^{1}$H-NMR (CDCl$_3$, 400 MHz): 7.99-7.46 (m, 6H), 4.96 (s, 1H), 4.79 (s, 1H), 3.91 (s, 3H), 3.89 (s, 3H), 2.64 (s, 3H), 2.60 (s, 3H), 1.43 (s, 3H) ppm.

Example 3.2

Preparation of 4-[5-(3,5-dichloro-phenyl)-4,4-difluoro-5-trifluoromethyl-4,5-dihydro-isoxazol-3-yl]-2-methyl-benzoic acid methyl ester

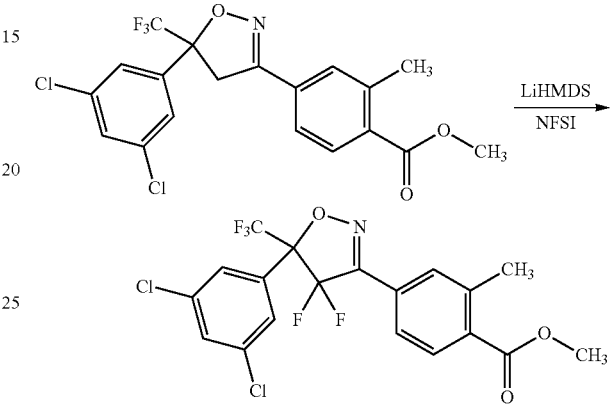

To a solution of 4-[5-(3,5-dichloro-phenyl)-5-trifluoromethyl-4,5-dihydro-isoxazol-3-yl]-2-methyl-benzoic acid methyl ester (made as described in EP 1,731,512) (519 mg) and N-fluorobenzenesulfonimide ("NFSI") (1.145 g) in dry tetrahydrofuran (10 ml) stirred under argon at 0° C., was added lithium bis(trimethylsilyl)amide ("LiHMDS") (1M in hexane) (3.6 ml). The solution was stirred at 0° C. for 4 hours then was allowed to stir at ambient temperature for 3 days. The reaction mixture was then quenched by addition of aqueous ammonium chloride (saturated) and was extracted with dichloromethane. The combined organic extracts were dried over magnesium sulfate and concentrated. The residue was purified by chromatography on silica gel (eluent: heptane/ethyl acetate 9:1) to give 4-[5-(3,5-dichloro-phenyl)-4,4-difluoro-5-trifluoromethyl-4,5-dihydro-isoxazol-3-yl]-2-methyl-benzoic acid methyl ester (140 mg) as a yellow oil. $^{1}$H-NMR (CDCl$_3$, 400 MHz): 8.00-7.98 (d, 1H), 7.72-7.51 (m, 5H), 3.92 (s, 3H), 2.64 (s, 3H) ppm.

Example 3.3

Preparation of 4-[5-(3,5-dichloro-phenyl)-4-methanesulfonyl-5-trifluoro-methyl-4,5-dihydro-isoxazol-3-yl]-2-methyl-benzoic acid methyl ester

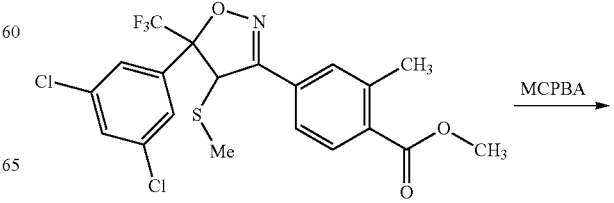

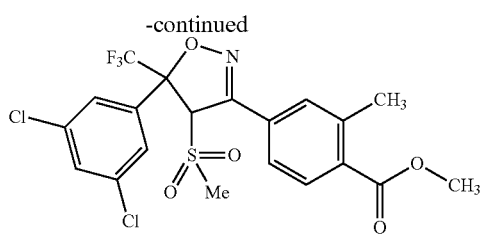

To a solution of 4-[5-(3,5-dichloro-phenyl)-5-trifluoromethyl-4-methylsulfanyl-4,5-dihydro-isoxazol-3-yl]-2-methyl-benzoic acid methyl ester (428 mg) in dichloromethane (15 ml) was added 3-chloroperoxybenzoic acid ("MCPBA") (500 mg) dropwise at ambient temperature. The reaction mixture was stirred for 5 hours then more 3-chloroperoxubenzoic acid ("MCPBA") (300 mg) was added dropwise. The reaction mixture was allowed to stand at ambient temperature for 3 days. Then more 3-chloroperbenzoic acid ("MCPBA") (100 mg) was added dropwise. The reaction mixture was allowed to stand at ambient temperature for another day. The reaction mixture was then treated with aqueous sodium metabisulfite (saturated) and extracted twice with dichloromethane. The combined organic phases were washed with brine, dried over sodium sulfate and concentrated. The residue was purified by chromatography on silica gel (eluent: heptane/diethyl ether 6:4) to give 4-[5-(3,5-dichloro-phenyl)-4-methanesulfonyl-5-trifluoromethyl-4,5-dihydro-isoxazol-3-yl]-2-methyl-benzoic acid methyl ester (300 mg) as white foam. $^1$H-NMR (CDCl$_3$, 400 MHz): 8.01-7.52 (m, 6H), 5.28 (s, 1H), 3.91 (s, 3H), 2.65 (s, 3H), 2.47 (s, 3H) ppm.

Example 3.4

Preparation of 4-[5-(3,5-dichloro-phenyl)-4-fluoro-5-trifluoromethyl-4,5-dihydro-isoxazol-3-yl]-2-methyl-benzoic acid tert-butyl ester

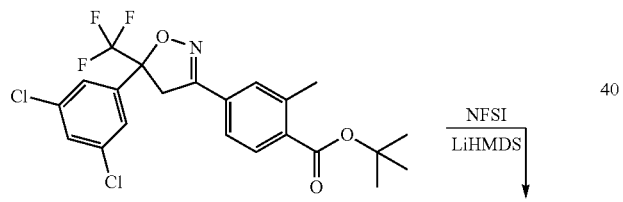

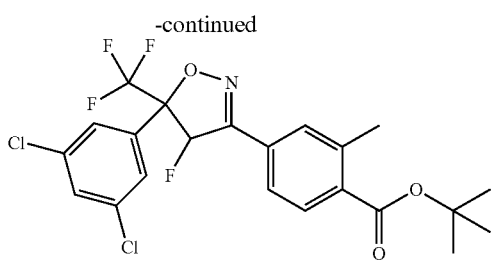

To a solution of 4-[5-(3,5-dichloro-phenyl)-5-trifluoromethyl-4,5-dihydro-isoxazol-3-yl]-2-methyl-benzoic acid tert-butyl ester (preparation of similar compounds described in, for example, EP 1,731,512) (500 mg) in tetrahydrofuran (6 ml) that was stirred at −78° C. for 15 minutes under argon, was slowly added lithium bis(trimethylsilyl)amide ("LiHMDS") (1M in hexane) (1.1 ml). The reaction mixture was stirred at −78° C. for 1.5 hours. Then N-fluorobenzenesulfonimide ("NFSI") (433 mg) was added quickly and the reaction mixture was stirred at −78° C. for 2 hours. The reaction was quenched by addition of aqueous ammonium chloride (saturated) at −78° C. tert-Butyl methyl ether ("TBME") was added and the phases were separated. The organic layer was washed successively with aqueous ammonium chloride (saturated) and brine, dried over magnesium sulfate and concentrated. The residue was purified by column chromatography on silica gel (eluent: dichloromethane/heptane 1:2) to give 4-[5-(3,5-dichloro-phenyl)-4-fluoro-5-trifluoromethyl-4,5-dihydro-isoxazol-3-yl]-2-methyl-benzoic acid tert-butyl ester (200 mg) as a colorless oil.

Example 3.5

Preparation of 4-[5-(3,5-dichloro-phenyl)-4-hydroxy-5-trifluoromethyl-4,5-dihydro-isoxazol-3-yl]-2-methyl-benzoic acid tert-butyl ester

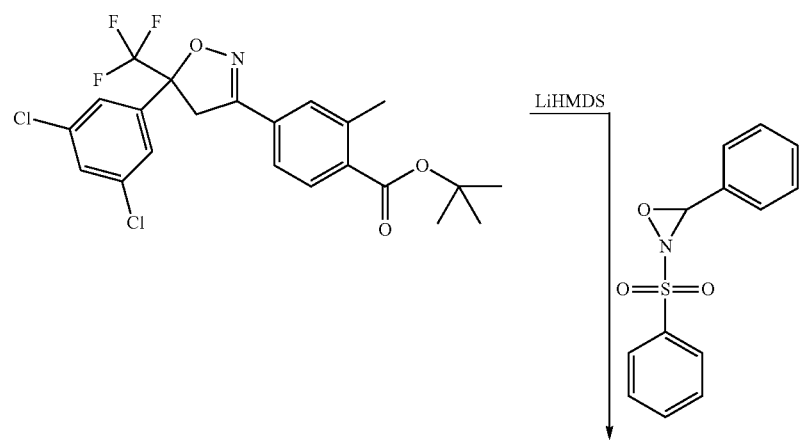

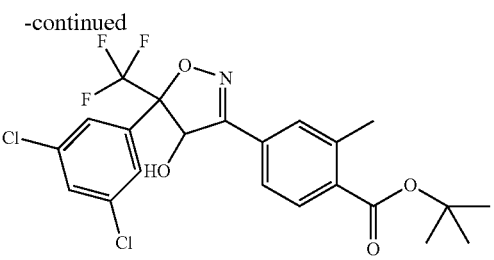

To a solution of 4-[5-(3,5-dichloro-phenyl)-5-trifluoromethyl-4,5-dihydro-isoxazol-3-yl]-2-methyl-benzoic acid tert-butyl ester (preparation of similar compounds described in, for example, EP 1,731,512) (2.83 g) in tetrahydrofuran (25 ml) that was stirred at −78° C. for 5 minutes under argon, was slowly added lithium bis(trimethylsilyl)amide ("LiHMDS") (1M in hexane) (6.9 ml). After 3 hours at −78° C., a cold (−20° C.) solution of 2-benzenesulfonyl-3-phenyl-oxaziridine (commercially available) (2.34 g) in tetrahydrofuran (10 ml) was added quickly. The temperature was kept below −65° C. for 4 hours and 30 minutes. The reaction was quenched by addition of aqueous ammonium chloride (saturated) at −78° C. tert-Butyl methyl ether ("TBME") was added and the phases were separated. The organic layer was washed successively with ammonium chloride and brine, dried over magnesium sulfate and concentrated. The residue was purified by column chromatography on silica gel (eluent: heptane/TBME 9:1) to give 4-[5-(3,5-dichloro-phenyl)-4-hydroxy-5-trifluoromethyl-4,5-dihydro-isoxazol-3-yl]-2-methyl-benzoic acid tert-butyl ester (738 mg) as a white solid.

TABLE A

Compounds of formula (Ia):

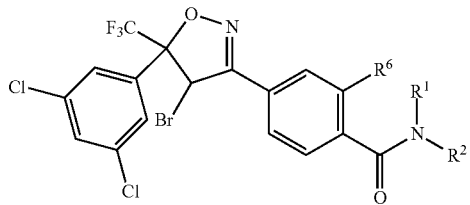

(Ia)

| Comp No. | R¹ | R² | R⁶ | RT (min) | [M + H]⁺ | LC-MS method |
|---|---|---|---|---|---|---|
| A1 | H | n-butyl- | Me | 1.94 | 550 | E |
| A2 | H | 2,2,2-trifluoro-ethyl- | Me | 2.09 | 576 | E |
| A3 | H | ethyl- | Me | 2.09 | 555 | E |
| A4 | H | 1-methoxy-prop-2-yl- | Me | 1.95 | 566 | E |
| A5 | H | (1H-benzimidazol-2-yl)-methyl- | Me | 1.65 | 624 | E |
| A6 | H | 3,3,3-trifluoro-propyl- | Me | 2.05 | 590 | E |
| A7 | H | but-2-yl- | Me | 2.05 | 550 | E |
| A8 | H | (tetrahydro-furan-2-yl)-methyl- | Me | 1.95 | 578 | E |
| A9 | H | phenyl-methyl- | Me | 2.16 | 584 | E |
| A10 | H | (2-fluoro-phenyl)-methyl- | Me | 2.10 | 602 | E |
| A11 | H | 1-phenyl-eth-1-yl- | Me | 217 | 598 | E |
| A12 | H | (4-methoxy-phenyl)-methyl- | Me | 2.07 | 614 | E |

TABLE A-continued

Compounds of formula (Ia):

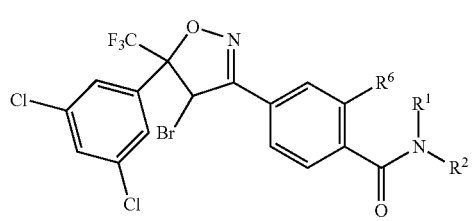

(Ia)

| Comp No. | R¹ | R² | R⁶ | RT (min) | [M + H]⁺ | LC-MS method |
|---|---|---|---|---|---|---|
| A13 | H | [4-(1H-pyrazol-1-yl)-phenyl]-methyl- | Me | 2.12 | 650 | E |
| A14 | H | (2-chloro-pyrid-5-yl)-methyl- | Me | 1.95 | 619 | E |
| A15 | H | 3-fluoro-phenyl- | Me | 2.16 | 589 | E |
| A16 | H | 4-(N,N-dimethyl-aminosulfonyl)-phenyl- | Me | 2.06 | 677 | E |
| A17 | H | 1,3-dimethyl-1H-pyrazol-5-yl- | Me | 1.95 | 589 | E |
| A18 | H | 4-methyl-thiazol-2-yl- | Me | 2.10 | 591 | E |
| A19 | H | 3-methyl-thietan-3-yl- | Me | 2.06 | 580 | E |
| A20 | H | 2-methyl-1-methylthio-prop-2-yl- | Me | 2.15 | 596 | E |
| A21 | H | (oxetan-2-yl)-methyl- | Me | 2.00 | 564 | E |
| A22 | H | thietan-3-yl- | Me | 1.95 | 566 | E |
| A23 | H | bicyclo[2.2.1]-heptan-2-yl- | Me | 2.16 | 588 | E |
| A24 | H | cyclobutyl- | Me | 2.07 | 548 | E |
| A25 | H | 1-oxo-thietan-3-yl-(isomer A) | Me | 2.05 | 585 | E |
| A26 | H | 1-oxo-thietan-3-yl-(isomer B) | Me | 2.04 | 585 | E |

TABLE B

Compounds of formula (Ib):

(Ib)

| Comp No. | R¹ | R² | R⁶ | RT (min) | [M + H]⁺ | LC-MS method |
|---|---|---|---|---|---|---|
| B1 | H | n-butyl- | Me | 4.06 | 507 | E |
| B2 | H | 2,2,2-trifluoro-ethyl- | Me | 3.99 | 533 | E |
| B3 | H | ethyl- | Me | 3.69 | 479 | E |
| B4 | H | (1H-benz-imidazol-2-yl)-methyl- | Me | 2.91 | 581 | E |
| B5 | H | 3,3,3-trifluoro-propyl- | Me | 3.98 | 547 | E |
| B6 | H | but-2-yl- | Me | 4.01 | 507 | E |
| B7 | H | (tetrahydro-furan-2-yl)-methyl- | Me | 3.74 | 535 | E |
| B8 | H | phenyl-methyl- | Me | 4.08 | 541 | E |
| B9 | H | (2-fluoro-phenyl)-methyl- | Me | 4.13 | 559 | E |
| B10 | H | 1-phenyl-eth-1-yl- | Me | 4.19 | 555 | E |
| B11 | H | (4-methoxy-phenyl)-methyl- | Me | 4.07 | 571 | E |
| B12 | H | 1,1-dioxo-thietan-3-yl- | Me | 3.53 | 555 | E |
| B13 | H | (2-chloro-pyrid-5-yl)-methyl- | Me | 3.91 | 576 | E |
| B14 | H | 3-fluoro-phenyl- | Me | 3.81 | 545 | E |
| B15 | H | 4-(N,N-dimethyl-aminosulfonyl)-phenyl- | Me | 4.18 | 634 | E |
| B16 | H | 1,3-dimethyl-1H-pyrazol-5-yl- | Me | 3.72 | 545 | E |
| B17 | H | 4-methyl-thiazol-2-yl- | Me | 4.12 | 548 | E |
| B18 | H | 3-methyl-thietan-3-yl- | Me | 4.06 | 537 | E |
| B19 | H | 2-methyl-1-methylthio-prop-2-yl- | Me | 4.27 | 553 | E |
| B20 | H | 1-oxo-thietan-3-yl- | Me | 3.3 | 539 | E |
| B21 | H | thietan-3-yl- | Me | 3.91 | 523 | E |
| B22 | H | bicyclo[2.2.1]-heptan-2-yl- | Me | 4.27 | 545 | E |
| B23 | H | cyclobutyl- | Me | 3.97 | 505 | E |

TABLE C

Compounds of formula (Ic):

(Ic)

| Comp No. | R¹ | R² | R⁶ | RT (min) | [M + H]⁺ | LC-MS method |
|---|---|---|---|---|---|---|
| C1 | H | (pyrid-2-yl)-methyl- | Me | 2.17 | 542/544 | E |

TABLE D

Compounds of formula (Id):

(Id)

| Comp No. | R¹ | R² | R⁶ | X | RT (min) | [M + H]⁺ | LC-MS method |
|---|---|---|---|---|---|---|---|
| D1 | H | n-butyl- | Me | S | 2.23 | 563/565 | F |
| D2 | H | n-butyl- | Me | SO₂ | 2.10 | 549/551 | F |
| D3 | H | thietan-3-yl- | Me | S | 2.16 | 579/581 | F |
| D4 | H | thietan-3-yl- | Me | SO₂ | 2.05 | 565/567 | F |

TABLE E

Compounds of formula (Ie):

(Ie)

| Comp No. | R¹ | R² | R⁶ | RT (min) | [M + H]⁺ | LC-MS method |
|---|---|---|---|---|---|---|
| E1 | H | n-butyl- | Me | 2.24 | 487/489 | F |
| E2 | H | thietan-3-yl- | Me | 2.14 | 547/549 | F |

TABLE F

Compounds of formula (I'a):

(I'a)

| Comp No. | R¹ | R² | RT (min) | [M + H]⁺ | LC-MS method |
|---|---|---|---|---|---|
| F1 | H | 2,2,2-trifluoro-ethyl- | 2.27 | 613/615 | E |
| F2 | H | ethyl- | 2.16 | 559/561 | E |
| F3 | H | n-butyl- | 2.3 | 587/589 | E |
| F4 | H | 1-methoxy-prop-2-yl- | 2.19 | 603/605 | E |
| F5 | H | (1H-benz-imidazol-2-yl)-methyl- | 1.7 | 661/663 | E |
| F6 | H | but-2-yl- | 2.29 | 587/589 | E |
| F7 | H | (tetrahydro-furan-2-yl)-methyl-) | 2.15 | 615/617 | E |
| F8 | H | phenyl-methyl- | 2.36 | 621/623 | E |

TABLE F-continued

Compounds of formula (I'a):

(I'a)

Structure: F₃C, Cl, Cl substituents on isoxazoline with Br, connected to naphthalene with C(=O)NR¹R²

| Comp No. | R¹ | R² | RT (min) | [M + H]⁺ | LC-MS method |
|---|---|---|---|---|---|
| F9 | H | (2-fluoro-phenyl)-methyl- | 2.37 | 639/641 | E |
| F10 | H | 1-phenyl-eth-1-yl- | 2.41 | 635/637 | E |
| F11 | H | (4-methoxy-phenyl)-methyl- | 2.35 | 651/653 | E |
| F12 | H | 1,1-dioxo-thietan-3-yl- | 2.06 | 635/637 | E |
| F13 | H | (2-chloro-pyrid-5-yl)-methyl- | 2.27 | 656/658 | E |
| F14 | H | 3-fluoro-phenyl- | 2.43 | 625/627 | E |
| F15 | H | 4-(N,N-dimethyl-aminosulfonyl)-phenyl- | 2.31 | 714/716 | E |
| F16 | H | 1,3-dimethyl-1H-pyrazol-5-yl- | 2.16 | 625/627 | E |
| F17 | H | 4-methyl-thiazol-2-yl- | 2.34 | 628/630 | E |
| F18 | H | 3-methyl-thietan-3-yl- | 2.35 | 617/619 | E |
| F19 | H | 2-methyl-1-methylthio-prop-2-yl- | 2.38 | 633/635 | E |
| F20 | H | 1-oxo-thietan-3-yl- | 1.94 | 619/621 | E |
| F21 | H | thietan-3-yl- | 2.15 | 603/605 | E |
| F22 | H | bicyclo[2.2.1]heptan-2-yl- | 2.46 | 625/627 | E |

TABLE G

Compounds of formula (Ig):

(Ig)

Structure with F₃C, Cl, Cl, F substituents on isoxazoline connected to phenyl with R⁶ and C(=O)NR¹R²

| Comp No. | R¹ | R² | R⁶ | RT (min) | [M + H]⁺ | LC-MS method |
|---|---|---|---|---|---|---|
| G1 | H | 1,1-dioxo-thietan-3-yl- | Me | 2.85 | 580 | B |
| G2 | H | 3-methyl-thietan-3-yl- | Me | 3.4 | 521 | B |
| G3 | H | thietan-3-yl- | Me | 3.22 | 507 | B |
| G4 | H | 1-oxo-thietan-3-yl- | Me | 2.55 | 523 | B |

TABLE H

Compounds of formula (Ih):

(Ih)

Structure with F₃C, Cl, Cl, HO substituents on isoxazoline connected to phenyl with R⁶ and C(=O)NR¹R²

| Comp No. | R¹ | R² | R⁶ | RT (min) | [M + H]⁺ | LC-MS method |
|---|---|---|---|---|---|---|
| H1 | H | 1,1-dioxo-thietan-3-yl- | Me | 2.43 | 537 | B |
| H2 | H | 3-methyl-thietan-3-yl- | Me | 2.93 | 519 | B |
| H3 | H | 1-oxo-thietan-3-yl- | Me | 2.17 | 521 | B |
| H4 | H | thietan-3-yl- | Me | 2.75 | 505 | B |

BIOLOGICAL EXAMPLES

This Example illustrates the pesticidal/insecticidal properties of compounds of formula (I) or formula (I').

Tests were performed as follows:

*Spodoptera Littoralis* (Egyptian Cotton Leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compound gave at least 80% control of *Spodoptera littoralis*: A1, A2, A3, A4, A5, A6, A7, A8, A9, A10, A11, A12, A13, A14, A15, A16, A17, A18, A19, A20, A21, A22, A23, A24, A25, A26, B1, B2, B3, B4, B5, B6, B7, B8, B9, B10, B11, B12, B13, B14, B15, B16, B17, B18, B19, B20, B21, B22, B23, C1, D1, D2, D3, E1, E2, F1, F3, F4, F5, F6, F7, F8, F9, F10, F11, F12, F13, F14, F15, F16, F17, F18, F19, F20, F21, F22, G1, G2, G3, G4, H1, H3, H4.

*Heliothis Virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compound gave at least 80% control of *Heliothis virescens*: A1, A2, A3, A4, A5, A6, A7, A8, A9, A10, A11, A12, A13, A14, A15, A16, A18, A19, A20, A21, A22, A23, A24, A25, A26, B1, B2, B3, B4, B5, B6, B7, B8, B9, B10, B11, B12, B13, B14, B15, B16, B17, B18, B19, B20, B21, B22, B23, C1, D1, D3, D4, E1, E2, F1, F3, F4, F5, F6, F7, F8, F9, F10, F11, F12, F13, F14, F15, F16, F17, F18, F19, F20, F21, F22, G1, G2, G3, G4, H1.

*Plutella Xylostella* (Diamond Back Moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compound gave at least 80% control of *Plutella xylostella*: A1, A2, A3, A4, A5, A6, A7, A8, A9, A10, A11, A12, A13, A14, A15, A16, A17, A18, A19, A20, A21, A22, A23, A24, A25, A26, B1, B2, B3, B4, B5, B6, B7, B8, B9, B10, B11, B12, B13, B14, B15, B16, B17, B18, B19, B20, B21, B22, B23, C1, D1, D2, D3, E1, E2, F1, F3, F4, F5, F6, F7, F8, F9, F10, F11, F12, F13, F14, F15, F16, F17, F18, F19, F20, F21, F22, G1, G2, G3, G4, H1, H2, H3, H4.

*Diabrotica Balteata* (Corn Root Worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compound gave at least 80% control of *Diabrotica balteata*: A1, A2, A3, A4, A5, A6, A7, A8, A9, A10, A11, A12, A13, A14, A15, A17, A18, A19, A20, A21, A22, A23, A24, A25, A26, B1, B2, B3, B4, B5, B6, B7, B8, B9, B10, B11, B12, B13, B15, B16, B17, B18, B19, B20, B21, B22, B23, C1, D1, D3, E1, E2, F1, F2, F4, F5, F6, F7, F8, F9, F10, F11, F12, F13, F14, F15, F16, F17, F18, F19, F20, F21, F22, G1, G2, G3, G4.

*Thrips Tabaci* (Onion Thrips):

Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality.

The following compounds gave at least 80% control of *Thrips tabaci*: A2, A3, A4, A6, A7, A8, A9, A10, A11, A12, A13, A14, A15, A19, A21, A22, A23, A24, A25, A26, B1, B2, B3, B5, B6, B7, B8, B9, B10, B11, B12, B13, B18, B19, B20, B21, B22, B23, E1, E2, F3, F4, F6, F7, F8, F9, F10, F11, F12, F14, F17, F18, F19, F20, F21, F22, G1, G2, G3, G4, H1, H3, H4.

*Tetranychus Urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compound gave at least 80% control of *Tetranychus urticae*: A1, A2, A3, A4, A5, A6, A7, A8, A9, A10, A11, A12, A13, A14, A15, A19, A20, A21, A22, A23, A24, A25, A26, B1, B2, B3, B4, B5, B6, B7, B8, B9, B10, B11, B12, B13, B16, B18, B19, B20, B21, B22, B23, C1, D3, D4, E1, E2, F4, F5, F7, F10, F11, F12, F13, F18, F19, F20, F21, G1, G2, G3, G4, H1, H3, H4.

The invention claimed is:

1. A compound of formula (I) or a compound of formula (I')

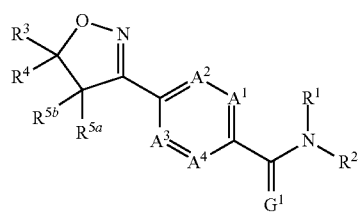

(I)

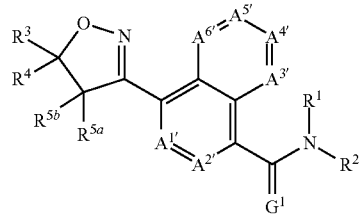

(I')

wherein
$A^1$, $A^2$, $A^3$ and $A^4$, or $A^{1'}$, $A^{2'}$, $A^{3'}$, $A^{4'}$, $A^{5'}$, and $A^{6'}$, are independently of each other C—H, C—$R^6$, or nitrogen;
$G^1$ is oxygen or sulfur;
$R^1$ is hydrogen, $C_1$-$C_8$alkyl, $C_1$-$C_8$alkoxy, $C_1$-$C_8$alkylcarbonyl-, or $C_1$-$C_8$alkoxycarbonyl-;
$R^2$ is the group (z):

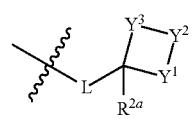

(z)

wherein L is a single bond or $C_1$-$C_6$ alkylene;
$R^{2a}$ is hydrogen, or $C_1$-$C_8$alkyl;
$Y^1$, $Y^2$ and $Y^3$ are independently of another $CR^{7a}R^{8a}$, C=O, C=N—$OR^{9a}$, N—$R^{9a}$, O, S, SO, $SO_2$, S=N—$R^{9a}$, or SO=N—$R^{9a}$, provided that at least one of $Y^1$, $Y^2$ or $Y^3$ is not $CR^{7a}R^{8a}$;
$R^{7a}$ and $R^{8a}$ are independently of another hydrogen, halogen, $C_1$-$C_8$alkyl, or $C_1$-$C_8$haloalkyl;
each $R^{9a}$ is independently hydrogen, cyano, nitro, $C_1$-$C_8$alkyl, $C_1$$C_8$haloalkyl, $C_1$-$C_8$alkylcarbonyl-, $C_1$-$C_8$haloalkylcarbonyl-, $C_1$-$C_8$alkoxycarbonyl-, $C_1$-$C_8$haloalkoxycarbonyl-, $C_1$-$C_8$alkylsulfonyl-, $C_1$-$C_8$haloalkylsulfonyl-, aryl-$C_1$-$C_4$alkyl- or aryl-$C_1$-$C_4$alkyl- wherein each aryl moiety is substituted by one to three $R^{11a}$, or is heteroaryl-$C_1$-$C_4$alkyl- or heteroaryl-$C_1$-$C_4$alkyl- wherein each heteroaryl moiety is substituted by one to three $R^{11a}$;
$R^{11a}$ is independently halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl-;
$R^3$ is $C_1$-$C_8$haloalkyl;
$R^4$ is aryl or aryl substituted by one to five $R^9$, or heteroaryl or heteroaryl substituted by one to five $R^9$;
$R^{5a}$ and $R^{5b}$ are, independently of each other, hydrogen, cyano, halogen, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, arylthio- or arylthio- wherein the aryl moiety is substituted by one to five $R^{10}$, arylsulfinyl- or arylsulfinyl- wherein the aryl moiety is substituted by one to five $R^{10}$, arylsulfonyl- or arylsulfonyl- wherein the aryl moiety is substituted by one to five $R^{10}$, heterocyclylthio- or heterocyclylthio- wherein the heterocyclyl moiety is substituted by one to five $R^{10}$, heterocyclylsulfinyl- or heterocyclylsulfinyl- wherein the heterocyclyl moiety is substituted by one to five $R^{10}$, or heterocyclylsulfonyl- or heterocyclylsulfonyl- wherein the heterocyclyl moiety is substituted by one to five $R^{10}$, $C_1$-$C_8$alkyl, $C_1$-$C_8$alkyl substituted by one to five $R^7$, $C_2$-$C_8$alkenyl, $C_2$-$C_8$alkynyl, $C_1$-$C_8$haloalkyl, $C_2$-$C_8$haloalkenyl, hydroxy, C₁-C₈alkoxy, C₃-C₈alkenyloxy, C₃-C₈alkynyloxy, or C₁-C₈haloalkoxy, provided that at least one of $R^{5a}$ and $R^{5b}$ is not hydrogen;

each $R^7$ is independently halogen, cyano, nitro, C₃-C₁₀cycloalkyl, C₃-C₁₀halocycloalkyl, hydroxy, C₁-C₈alkoxy, C₁-C₈haloalkoxy, mercapto, C₁-C₈alkylthio-, C₁-C₈haloalkylthio-, C₁-C₈alkylsulfinyl-, C₁-C₈haloalkylsulfinyl-, C₁-C₈alkylsulfonyl-, or C₁-C₈haloalkylsulfonyl-; and each $R^6$, $R^9$ and $R^{10}$ is independently halogen, cyano, nitro, C₁-C₈alkyl, C₁-C₈haloalkyl, C₃-C₁₀cycloalkyl, C₃-C₁₀halocycloalkyl, C₂-C₈alkenyl, C₂-C₈haloalkenyl, C₂-C₈alkynyl, C₂-C₈haloalkynyl, hydroxy, C₁-C₈alkoxy, C₁-C₈haloalkoxy, mercapto, C₁-C₈alkylthio-, C₁-C₈haloalkylthio-, C₁-C₈alkylsulfinyl-, C₁-C₈haloalkylsulfinyl-, C₁-C₈alkylsulfonyl-, C₁-C₈haloalkylsulfonyl-, C₁-C₈alkylcarbonyl-, C₁-C₈alkoxycarbonyl-, aryl or aryl itself substituted by one to five substituents independently selected from halogen, C₁-C₄alkyl, C₁-C₄haloalkyl, C₁-C₄alkoxy, or C₁-C₄haloalkoxy, or heterocyclyl or heterocyclyl itself substituted by one to five substituents independently selected from halogen, C₁-C₄alkyl, C₁-C₄haloalkyl, C₁-C₄alkoxy, or C₁-C₄haloalkoxy;

or a salt or N-oxide thereof.

2. A compound of formula (I) according to claim 1 wherein $A^1$, $A^2$, $A^3$ and $A^4$ are independently C—H or C—$R^6$.

3. A compound of formula (I') according to claim 1 wherein $A^{1'}$, $A^{2'}$, $A^{3'}$, $A^{4'}$, $A^{5'}$ and $A^{6'}$ are independently C—H or C—$R^6$.

4. A compound of formula (I) or a compound of formula (I') according to claim 1 wherein $G^1$ is oxygen.

5. A compound of formula (I) or a compound of formula (I') according to claim 1 wherein $R^1$ is hydrogen, methyl, ethyl, methylcarbonyl-, or methoxycarbonyl-.

6. A compound of formula (I) or a compound of formula (I') according to claim 1 wherein L is a single bond;

$Y^1$, $Y^2$ and $Y^3$ are independently of another $CR^{7a}R^{8a}$, N—$R^{9a}$, O, S, SO, SO₂, S═N—$R^{9a}$, or SO═N—$R^{9a}$, provided that only one of $Y^1$, $Y^2$ or $Y^3$ is not $CR^{7a}R^{8a}$;

$R^{2a}$ is hydrogen or methyl;

$R^{7a}$ and $R^{8a}$ are independently of another hydrogen, halogen C₁-C₄ alkyl or C₁-C₄ haloalkyl; and $R^{9a}$ is hydrogen, halogen C₁-C₄ alkyl or C₁-C₄ haloalkyl.

7. A compound of formula (I) or a compound of formula (I') according to claim 1 wherein $R^2$ is thietanyl, oxo-thietanyl or dioxo-thietanyl each optionally substituted by one to five $R^8$.

8. A compound of formula (I) or a compound of formula (I') according to claim 1 wherein $R^2$ is thietanyl, oxo-thietanyl or dioxo-thietanyl, each optionally substituted by one to five $R^8$, and each linked via the 3-position.

9. A compound of formula (I) or a compound of formula (I') according to claim 1 wherein $R^3$ is chlorodifluoromethyl or trifluoromethyl.

10. A compound of formula (I) or a compound of formula (I') according to claim 1 wherein $R^4$ is aryl or aryl substituted by one to five $R^9$.

11. A compound of formula (I) or a compound of formula (I') according to claim 1 wherein $R^{5a}$ and $R^{5b}$ are, independently of each other, hydrogen, cyano, halogen, C₁-C₈alkylthio-, C₁-C₈haloalkylthio-, C₁-C₈alkylsulfinyl-, C₁-C₈haloalkylsulfinyl-, C₁-C₈alkylsulfonyl-, C₁-C₈haloalkylsulfonyl-, arylthio- wherein the aryl moiety is substituted by one to five $R^{10}$, arylsulfinyl- or arylsulfinyl- wherein the aryl moiety is substituted by one to five $R^{10}$, arylsulfonyl- or arylsulfonyl- wherein the aryl moiety is substituted by one to five $R^{10}$, heterocyclylthio- or heterocyclylthio- wherein the heterocyclyl moiety is substituted by one to five $R^{10}$, heterocyclylsulfinyl- or heterocyclylsulfinyl- wherein the heterocyclyl moiety is substituted by one to five $R^{10}$, or heterocyclylsulfonyl- or heterocyclylsulfonyl- wherein the heterocyclyl moiety is substituted by one to five $R^{10}$, C₁-C₈alkyl, C₂-C₈alkenyl, C₂-C₈alkynyl, C₁-C₈haloalkyl, C₂-C₈haloalkenyl, hydroxy, C₁-C₈alkoxy, C₃-C₈alkenyloxy, C₃-C₈alkynyloxy, or C₁-C₈haloalkoxy, provided that at least one of $R^{5a}$ and $R^{5b}$ is not hydrogen.

12. A compound of formula (I) or a compound of formula (I') according to claim 1 wherein $R^{5a}$ is halogen, C₁-C₈alkylthio-, C₁-C₈haloalkylthio-, C₁-C₈alkylsulfinyl-, C₁-C₈haloalkylsulfinyl-, C₁-C₈alkylsulfonyl-, C₁-C₈haloalkylsulfonyl-, C₁-C₈alkyl, C₂-C₈alkenyl, C₂-C₈alkynyl, C₁-C₈haloalkyl, C₂-C₈haloalkenyl, most preferably halogen, C₁-C₈alkylthio- or C₁-C₈alkyl.

13. A compound of formula (I) or a compound of formula (I') according to claim 1 wherein $R^{5a}$ is hydroxy.

14. A compound of formula (I) or a compound of formula (I') according to claim 1 wherein $R^{5b}$ is halogen or hydrogen.

15. A compound of formula (I) or a compound of formula (I') according to claim 1, wherein each $R^6$ is independently bromo, chloro, fluoro, cyano, nitro, methyl, ethyl, trifluoromethyl, methoxy, difluoromethoxy, or trifluoromethoxy;

each $R^7$ is independently halogen, cyano, nitro, hydroxy, C₁-C₈alkoxy, C₁-C₈haloalkoxy, mercapto, C₁-C₈alkylthio-, C₁-C₈haloalkylthio-;

each $R^8$ is independently bromo, chloro, fluoro, cyano, nitro, methyl, ethyl, trifluoromethyl, methoxy, difluoromethoxy, or trifluoromethoxy;

each $R^9$ is independently bromo, chloro, fluoro, trifluoromethyl, methoxy, or methylthio; and each $R^{10}$ is independently bromo, chloro, fluoro, cyano, nitro, methyl, ethyl, trifluoromethyl, methoxy, difluoromethoxy, or trifluoromethoxy.

16. A compound according to claim 1 wherein the compound of formula (I) or compound of formula (I') is a compound of formula ($I^a$) or a compound of formula ($I^b$):

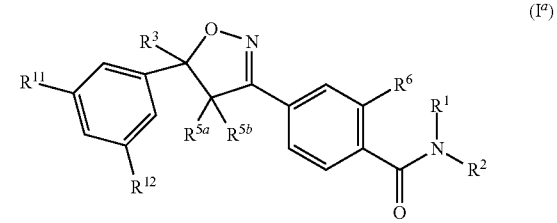

($I^a$)

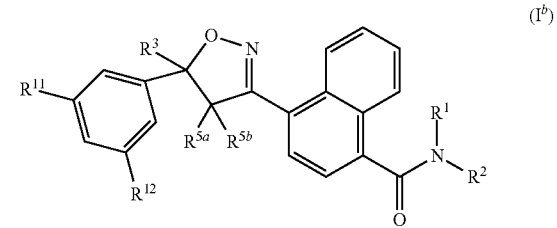

($I^b$)

wherein $R^1$ is hydrogen, methyl, or ethyl;

$R^2$ is thietanyl, oxo-thietanyl or dioxo-thietanyl, each linked to the nitrogen atom via the 3-position, and each optionally substituted by halogen, C₁-C₄ alkyl or C₁-C₄ haloalkyl;

$R^3$ is chlorodifluoromethyl or trifluoromethyl;

$R^{5a}$ is halogen, hydroxy, $C_1$-$C_4$ alkyl, $C_1$-$C_4$ haloalkyl, $C_1$-$C_4$ alkylthio, $C_1$-$C_4$ haloalkylthio, $C_1$-$C_4$ alkylsulfonyl, $C_1$-$C_4$ haloalkylsulfonyl, $C_1$-$C_4$ alkylsulfinyl, or $C_1$-$C_4$ haloalkylsulfinyl;

$R^{5b}$ is hydrogen or halogen;

$R^6$ is $C_1$-$C_4$ alkyl or $C_1$-$C_4$ haloalkyl; and $R^{11}$ and $R^{12}$ are independently hydrogen, halogen $C_1$-$C_4$ alkyl or $C_1$-$C_4$ haloalkyl.

17. A compound of formula ($I^a$) or a compound of formula ($I^b$) according to claim 16, wherein $R^1$ is hydrogen;

$R^2$ is thietanyl, oxo-thietanyl or dioxo-thietanyl, each linked via the 3-position, and each optionally substituted at the 3 position by methyl;

$R^3$ is trifluoromethyl;

$R^{5a}$ is halogen, hydroxyl, methyl, methylthio, methylsulfinyl or methylsulfonyl;

$R^{5b}$ is hydrogen or halogen; and $R^{11}$ and $R^{12}$ are independently fluorine, chlorine or bromine.

18. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) or of a compound of formula (I') as defined in claim 1.

19. An insecticidal, acaricidal, nematicidal or molluscicidal composition comprising an insecticidally, acaricidally, nematicidally or molluscicidally effective amount of a compound of formula (I) or of a compound of formula (I') as defined in claim 1.

* * * * *